US012338196B2

United States Patent
Hanes, Jr. et al.

(10) Patent No.: US 12,338,196 B2
(45) Date of Patent: *Jun. 24, 2025

(54) HEXASUBSTITUTED BENZENES, SURFACES MODIFIED THEREWITH, AND ASSOCIATED METHODS

(71) Applicant: Countertrace, LLC, Manvel, TX (US)

(72) Inventors: Robert E. Hanes, Jr., Missouri City, TX (US); Richard L. Pettys, Pearland, TX (US); David M. Headley, Pearland, TX (US); Paul T. Hoopingarner, Missouri City, TX (US)

(73) Assignee: COUNTERTRACE, LLC, Manvel, TX (US)

( * ) Notice: Subject to any disclaimer, the term of this patent is extended or adjusted under 35 U.S.C. 154(b) by 822 days.

This patent is subject to a terminal disclaimer.

(21) Appl. No.: 17/584,577

(22) Filed: Jan. 26, 2022

(65) Prior Publication Data

US 2022/0144733 A1   May 12, 2022

Related U.S. Application Data

(63) Continuation of application No. 17/190,694, filed on Mar. 3, 2021, now Pat. No. 11,267,773, which is a continuation of application No. PCT/US2020/050096, filed on Sep. 10, 2020.

(60) Provisional application No. 62/898,182, filed on Sep. 10, 2019, provisional application No. 62/898,258, filed on Sep. 10, 2019, provisional application No. 62/898,201, filed on Sep. 10, 2019.

(51) Int. Cl.

| | |
|---|---|
| C07C 22/04 | (2006.01) |
| C07C 235/60 | (2006.01) |
| C07C 247/10 | (2006.01) |
| C07D 249/06 | (2006.01) |
| C07D 303/36 | (2006.01) |
| C07D 405/14 | (2006.01) |

(52) U.S. Cl.
CPC ............ *C07C 22/04* (2013.01); *C07C 235/60* (2013.01); *C07C 247/10* (2013.01); *C07D 249/06* (2013.01); *C07D 303/36* (2013.01); *C07D 405/14* (2013.01)

(58) Field of Classification Search
CPC ..... C07C 22/04; C07C 235/60; C07C 247/10; C07C 219/22; C07D 249/06; C07D 303/36; C07D 405/14; C07D 303/08
See application file for complete search history.

(56) References Cited

U.S. PATENT DOCUMENTS

| | | | |
|---|---|---|---|
| 4,448,935 A | 5/1984 | Iovine et al. | |
| 4,650,910 A | 3/1987 | Henneke et al. | |

(Continued)

FOREIGN PATENT DOCUMENTS

| | | | |
|---|---|---|---|
| CN | 102295728 A | 12/2011 | |
| CN | 102500290 | 6/2012 | |

(Continued)

OTHER PUBLICATIONS

Gavette et al. Hydrogen Bonding vs. Steric Gearing in a Hexasubstituted Benzene (J. Org. Chem. 73: 3582-3584). (Year: 2008).*

(Continued)

*Primary Examiner* — Joseph K McKane
*Assistant Examiner* — Meghan C Heasley
(74) *Attorney, Agent, or Firm* — Foley & Lardner LLP

(57) ABSTRACT

Phenyl rings provide a robust scaffold for molecular design, given the limited number of ring carbon atoms and the fixed geometry in between. However, it can be difficult to form highly substituted phenyl rings suitable for covalent attachment of multiple moieties thereto. Moreover, binding phenyl rings to a surface in a fixed geometry may be difficult. Hexasubstituted benzenes having certain structural features may alleviate the foregoing difficulties by providing versatile groups for further functionalization and surface attachment. Such hexasubstituted benzenes may have a structure of

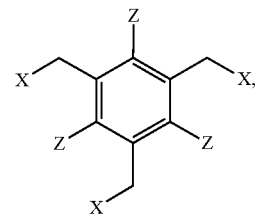

in which each X is independently Cl, Br or $N_3$, and each Z is independently —$CH(Br)CH_3$, —$CH(N_3)CH_3$, —$CH=CH_2$, —$CH_2CH_3$, —$CH_2CH_2SiR'_3$ (R'=hydrocarbyl), or

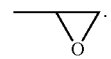

Alternating groups in the hexasubstituted benzenes may be directed toward opposite faces of the phenyl ring, such that orthogonal reactive groups are directed toward the opposite faces. Certain groups may facilitate surface attachment of the hexasubstituted benzenes.

20 Claims, 6 Drawing Sheets

(56) References Cited

U.S. PATENT DOCUMENTS

| | | | |
|---|---|---|---|
| 4,668,739 | A | 5/1987 | Berdahl et al. |
| 4,857,580 | A | 8/1989 | Patzschke et al. |
| 5,073,603 | A | 12/1991 | Eikenberry et al. |
| 5,841,001 | A | 11/1998 | Tanaka et al. |
| 5,895,796 | A | 4/1999 | Mouri et al. |
| 5,981,807 | A | 11/1999 | Kodama et al. |
| 6,048,732 | A | 4/2000 | Anslyn et al. |
| 6,794,448 | B2 | 9/2004 | Sakuma |
| 6,812,276 | B2 | 11/2004 | Yeager |
| 6,946,070 | B2 | 9/2005 | Hammen et al. |
| 8,791,188 | B2 | 7/2014 | Ghandi |
| 2004/0063870 | A1 | 4/2004 | Burns et al. |
| 2005/0124707 | A1 | 6/2005 | Eldridge et al. |
| 2006/0068317 | A1 | 3/2006 | Klei et al. |
| 2008/0099715 | A1 | 5/2008 | Adams et al. |
| 2009/0215646 | A1 | 8/2009 | Anslyn et al. |
| 2012/0271064 | A1 | 10/2012 | Henninger et al. |
| 2013/0157905 | A1 | 6/2013 | Saini et al. |
| 2016/0339412 | A1 | 11/2016 | Rasmussen et al. |
| 2018/0065904 | A1 | 3/2018 | Pappo et al. |
| 2018/0304684 | A1 | 10/2018 | Rannoux et al. |

FOREIGN PATENT DOCUMENTS

| | | |
|---|---|---|
| CN | 105693918 | 6/2016 |
| CN | 109206623 | 1/2019 |
| DE | 10355169 A1 | 6/2005 |
| JP | S62-153754 A | 7/1987 |
| JP | 2005-170823 A | 6/2005 |
| KR | 1020060104662 | 10/2006 |
| WO | WO-2009/119513 A1 | 10/2009 |
| WO | WO-2011/002850 | 1/2011 |
| WO | WO-2013/118100 | 8/2013 |

OTHER PUBLICATIONS

EP Search Report from corresponding EP Application No. 20863349 mailed Nov. 8, 2023.

Hopff, Heinrich and A. Wick. "Zur Kenntnis der Hexaalkylbenzole. 3. Mitteilung. Über einen neuen Kohlenwasserstoff C18H24 (Hexaäthylidencyclohexan)." Helvetica Chimica Acta 44 (1961): 380-386.

Hopff, H. and Wick, A.K. (1961), On the Knowledge of Hexaalkylbenzenes. II. Notice. Side chain halogenations of hexaethylbenzene. Helvetica Chimica Acta 44 (1961): 19-44.

Hennrich, G. and Anslyn, E.V. (2002), 1,3,5-2,4,6-Functionalized, Facially Segregated Benzenes—Exploitation of Sterically Predisposed Systems in Supramolecular Chemistry. Chem. Eur. J., 8: 2218-2224.

Meier, Herbert et al. "Synthesis of Hexastyrylbenzenes." Synthesis 1997 (1997): 276-278.

Sha, Chin-Kang. et al. "A retro-malonate addition reaction: synthesis of 3,4-condensed heteroaromatic pyrroles." Journal of The Chemical Society, Chemical Communications (1988): 1081-1083.

Collins, Byron E et al: "Pattern-Based Peptide Recognition", Chemistry—A European Journal, John Wiley & Sons, Inc, DE, vol. 13, No. 17, May 8, 2007 (May 8, 2007), pp. 4700-4708, XP071826202, ISSN: 0947-6539, DOI: 10.1002/CHEM.200700153.

European Search Report on EP20864230.6 dated Oct. 10, 2023 (9 pages).

International Search Report and Written Opinion on PCT/US2020/050108 dated Dec. 24, 2020 (11 pages).

Lavigne J J et al: "Single Analyte to Multi-Analyte Fluorescence Sensors", Proceedings of SPIE, IEEE, US, vol. 3602, Jan. 1, 1999 (Jan. 1, 1999), pp. 220-231, XP000863546, DOI: 10.1117/12.347545, ISBN: 978-1-62841-730-2.

Wright, Aaron T. et al: "Differential receptor arrays and assays for solution-based molecular recognition", Chemical Society Reviews, vol. 35, No. 1, Jan. 1, 2006 (Jan. 1, 2006), pp. 14-28, XP055718322,UK, ISSN: 0306-0012, DOI: 10.1039/B505518K.

Anslyn, E.V., "Supramolecular Analytical Chemistry," J. Org. Chem., 2007, pp. 687-699, 72.

Bayramoglu, G., et al., "Ethylenediamine grafted poly{glycidylmethacrylate-co-methylmethacrylate) adsorbent for removal of chromate anions," Separation and Purification Technology, 2005, pp. 192-199, 45.

Caykara, T., et al., "A New Type of Poly{glycidyl methacrylate) Microbeads with Surface Grafted Iminodiacetic Acid: Synthesis and Characterization," Polymer Bulletin, 2008, pp. 311-318, 61.

International Search Report and Written Opinion for PCT/US2020/041407, published Oct. 30, 2020.

International Search Report and Written Opinion for PCT/US2020/041417, published Oct. 26, 2020.

Kilway, K.V., et al., "Control of functional group proximity and direction by conformational networks: synthesis and stereodynamics of persubstituted arenes," Tetrahedron, 2001, pp. 3615-3627, 57.

Lee, S.G., et al., "Amine-functionalized macroporous microspheres for HF removal from aqueous solution," AIP Conference Proceedings, 2016, Article No. 140005, pp. 1-5, 1713.

Liu, C., et al., "Functionalization of adsorbent with different aliphatic polyamines for heavy metal ion removal: Characteristics and performance," J. Colloid and Interface Sci., 2010, pp. 454-460, 345.

Liu, C., et al., "Diethylenetriamine-grafted poly{glydicyl methacrylate) adsorbent for effective copper ion adsorption," J Colloid and Interface Sci., 2006, pp. 99-108, 303.

Nastasovic, A., et al., "Kinetics of hexavalent chromium sorption on amino-functionalized macroporous glycidyl methacrylate copolymer," J. Hazardous Mat., 2009, pp. 153-159, 171.

PubChem ID 138452, "1,3,5-trichloro-2,4,6-trimethylbenzene," created Mar. 26, 2005.

Radova, Z. et al., "Sorption of Pd(II) from aqueous solutions of chlorocomplexes by the copolymer of glycidylmethacrylate and ethylenedimethacrylate modified with ethylenediamine. The structure of complexes," Die Angewandte Makromolekulare Chemie, 2003, pp. 55-62, 81.

Ross, S.D., et al., "Preparation of 1,3,5-trivinyl-2,4,6-trichlorobenzene and its copolymerization with Styrene," J. Poly. Sci., 1952, pp. 219-228, 9, {Abstract).

Sasaki, S., et al., "Design and synthesis of preorganized tripodal fluororeceptors based on hydrogen bonding of thiourea groups for optical phosphate ion sensing," J_ Chem. Soc., Perkin Trans. 2, 2001, pp. 2309-2313.

Wallace, K.J., et al., "Preparation of 1,3,5-Tris{aminomethyl)-2,4,6-triethylbenzene from Two Versatile 1,3,5-Tri (halosubstituted) 2,4,6-Triethylbenzene Derivatives," Synthesis, 2005, pp. 2080-2083.

Wang, H., et al., "Polymer monoliths with chelating functionalities for solid phase extraction of metal ions from water," Journal of Chromatography A, 2014, pp. 128-134, 1343.

Yan, X., et al., "Highly Monodisperse Sub-Microspherical Poly{glycidyl methacrylate) Nanocomposites with Highly Stabilized Gold Nanoparticles," Macromol. Chem. Phys., 2014, pp. 1098-1106, 215.

* cited by examiner

HEXASUBSTITUTED BENZENES, SURFACES MODIFIED THEREWITH, AND ASSOCIATED METHODS

CROSS-REFERENCE TO RELATED APPLICATIONS

The present application is a continuation of U.S. patent application Ser. No. 17/190,694, filed on Mar. 3, 2021, which is a continuation of International Patent Application PCT/US2020/050096, filed on Sep. 10, 2020, which claims the benefit of priority under 35 U.S.C. § 119 from U.S. Provisional Patent Applications 62/898,182, 62/898,201, and 62/898,258, each filed on Sep. 10, 2019 and incorporated herein by reference in its entirety.

STATEMENT REGARDING FEDERALLY SPONSORED RESEARCH OR DEVELOPMENT

Not applicable.

BACKGROUND

Detection and quantification of various analytes may be conducted in conjunction with numerous processes, such as quality and process control, medical diagnostic testing, environmental monitoring, and the like. Analytes to be monitored under a given set of circumstances may exhibit wide structural and functional diversity and include substances such as, but not limited to, microorganisms, cells, trace metals, explosive molecules, drug molecules, poisons, solvents, other chemicals, metabolites, and the like. These analytes and many others may be detected through the physical measurement of properties resulting from chemical interactions of analytes with a chemical receptor (sensing functionality) through mechanisms including, but not limited to, charge pairing, charge transfer, hydrophobic effects, reversible covalent bond formation, pH effects, electrochemical behavior, and other processes associated with molecular recognition. Such chemical interactions may be referred to herein as "molecular association." This type of pairwise interaction is similar to the 'lock and key' paradigm commonly used to explain the interactions between biological molecules and natural receptors. The chemical receptor may constitute a portion of a larger molecule or a whole molecule itself. For example, the chemical receptor may recognize strands of amino acids, proteins, sugars, lipids and/or nucleotide sequences that may or may not be fragments of DNA, RNA and general pairings associated with such biological systems. Ligands having at least partial specificity for particular metal ions may also comprise at least a portion of a chemical receptor in some instances.

Suitable procedures may need to be developed and validated for effectively assaying a given analyte of interest, particularly when using general purpose laboratory equipment such as spectrophotometers and electrochemical detection techniques. In some instances, it can be desirable to employ specifically configured media or sensors for conducting analyses of certain analytes, particularly when performing repeated measurements at high throughput, such as during process control and/or monitoring. Sensors or similar media configured for analyzing for a particular analyte of interest may simplify technological challenges associated with such analyses, especially for users having limited laboratory skills and/or for testing in field environments with limited laboratory capabilities. Plate-based analyses featuring specifically functionalized well media may be particularly desirable sensor constructs for conducting multiple analyses in parallel in a high-throughput manner. Flow-through sensors may be desirable sensor constructs for continuous process monitoring and/or control. Flow-through sensors may comprise an active area containing functionality for assaying an analyte of interest, without immersion of the active area in a fluid comprising the analyte. Instead, in a flow-through sensor, fluid is received, passes across the active area as a dynamic stream, and is then discharged.

The sensing functionality in chemical sensors may comprise a particular molecular structure or group of molecular structures that is/are complementary to an analyte of interest, such that the analyte undergoes a specific molecular association with the sensing functionality. Detection of the molecular association and the magnitude thereof may allow an analyte's presence to be determined and the amount thereof to be quantified based upon a measurable physical property. The sensing functionality may be specific to a single analyte of interest or to a range of analytes of a particular type. The molecular association between the analyte of interest and the sensing functionality may be covalent or non-covalent in nature.

When conducting analyses, it may be desirable to covalently bond a suitable sensing functionality to a surface. Covalent bonding of a sensing functionality to a surface may limit loss of the sensing functionality to the surrounding environment, thereby affording a more robust sensing system. Covalent bonding may be particularly desirable for continuous and flow-through sensing systems to facilitate dynamic evaluation of flowing streams, since the sensing functionality remains adhered to the sensor and available for prolonged detection of an analyte. In addition, covalent bonding of a sensing functionality to a surface may provide operational advantages for shelf life and storage. Specifically, various precursors containing a sensing functionality may be stored in a non-covalently bound state and undergo subsequent bonding to a surface at a desired time to form the active portion of a sensor. Indeed, with strategically chosen functionality for promoting covalent bond formation, a chemical sensor may be robotically applied to a surface during manufacture and eliminate the intervention of a technician, who is otherwise required to load a plate with the correct reagents for testing. Particular functionality may undergo essentially instantaneous bonding to an appropriately functionalized surface. Further, this feature may permit the fabrication of complex chemical sensors ready for near-immediate analyses in a high-throughput and/or combinatorial manner, thereby eliminating the usual practice of adding fresh testing reagent to a test plate or well immediately prior to an analysis. That is, precursors to surface-bound sensing functionalities may be stockpiled and rapidly deployed to prepare sensors configured for performing analyses, rather than being stockpiled by a supplier or custom-prepared just prior to use, as in many plate-based analyses. Despite the desirability of covalently assembled, surface-bound chemical sensors, such features may oftentimes be difficult to achieve in practice.

Outside the sensor realm, it can also be desirable to modify the properties of a surface for a number of application-specific reasons. As non-limiting examples, a surface may be modified to change one or more of chemical reactivity, hydrophilicity/hydrophobicity, coefficient of friction, surface roughness, contact angle, optical properties (e.g., absorbance, fluorescence, luminescence, phosphorescence, or combinations such as FRET (fluorescence-resonance energy transfer)), biocompatibility, antimicrobial properties, and similar features of the surface. Certain surface modifications may also promote molecular recognition.

Although surface attachment of a sensing functionality or other type of surface-modifying functionality may be desirable and accomplished through a wide range of chemical reactions, there may be several complicating issues when performing analyses using a surface-bound sensing functionality. For example, a linker moiety appending a sensing functionality to a surface may exhibit a high degree of conformational flexibility, thereby affording a wide number of degrees of freedom and positioning the sensing functionality in various possible orientations. The variable orientations of the sensing functionality may alter the extent to which the sensing functionality interacts with an analyte of interest, thereby changing the magnitude of the measured response and leading to potential measurement inaccuracies when analyzing for certain analytes. Similar types of property variability arising from conformational flexibility may also occur when modifying a surface for other application-specific purposes. For example, variable coverage density of a functionalizing group upon a surface may be similarly problematic for producing a functionalized surface having uniform properties. At present, there are very few options for introducing functional modifications to a surface uniformly and in an orientationally controlled manner. Surface modifications introduced through covalent bond formation while still maintaining uniform surface coverage and orientational control are even rarer still.

It is generally accepted in supramolecular chemistry that 'preorganization' minimizes disfavorable entropy from binding free energies, for the 'entropy price' is paid in the synthesis. This concept is readily exemplified by the simple example of a crown ether or other macromolecular binding construct. When applied to a sensing functionality, analyte binding usually does not require a large entropy price, for the supramolecular assembly configured for interacting with an analyte of interest usually undergoes minimal conformational change when binding the analyte. Entropic contributions may also be decreased by limiting the number of degrees of freedom available by attaching a supramolecular assembly to a surface. Surface attachment may minimize internal rearrangements and create a more favorable analyte binding environment on the whole, in addition to affording the other advantages mentioned above. With a surface-bound sensing functionality, concentration therefore becomes a time-dependent quantity to monitor dynamic changes within a fluid of interest.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
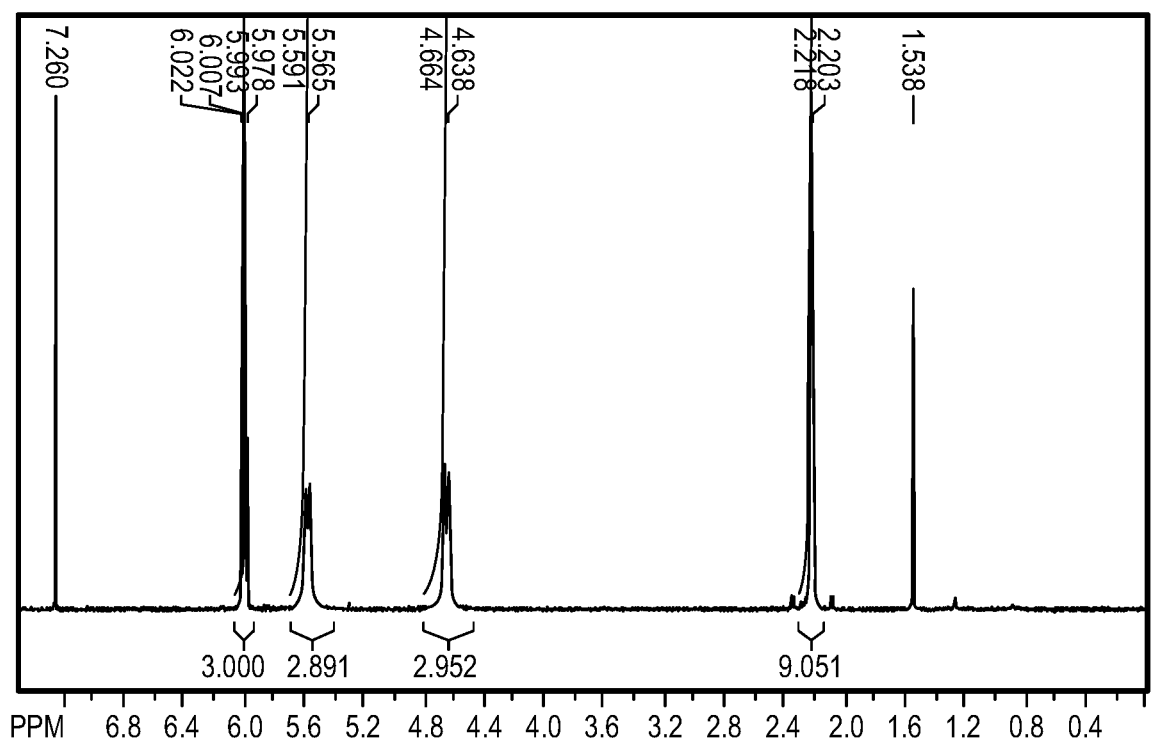
FIGS. 1 and 2 are $^1$H and $^{13}$C NMR spectra of 1,3,5-tris(halomethyl)-2,4,6-tris(α-bromoethyl)benzene in CDCl$_3$, respectively.

The present disclosure generally describes hexasubstituted benzenes that may serve as robust molecular scaffolds for attachment of various entities to a surface, particularly one or more sensing functionalities, and, more specifically, hexasubstituted benzenes and surface-attached hexasubstituted benzenes and methods for production and use thereof. Modified surfaces functionalized with a hexasubstituted benzene are also disclosed herein.

As discussed above, functionalization of surface may be difficult to control, such as when attaching sensing functionalities to a surface during fabrication of a sensor, plate or flow-through testing apparatus. As a non-limiting example, functionalizing groups may reside in a range of available configurations when covalently bound to a surface. Variable surface coverage may also be an issue. Inconsistent surface coverage and/or conformational variability of functionalizing groups upon a surface may result in surface irregularities and differing surface properties in some instances, which may lead to inconsistent sensing performance in the case of sensing functionalities. Thus, even if suitable sensing functionalities and chemistry to bond the sensing functionalities to a given type of surface, there can still be issues of sensing accuracy due to the range of available orientations once the sensing functionalities are surface bound.

The present disclosure demonstrates that certain hexasubstituted benzenes may serve as robust and versatile molecular scaffolds for promoting covalent attachment of a range of sensing functionalities or other types of functional modifications to various types of surfaces. Due to steric crowding around the phenyl ring, hexasubstituted benzenes may exhibit a locked conformation in which substituents at alternating ring carbon atoms are directed toward opposite faces of the phenyl ring. For purposes of the present disclosure, a locked conformation also includes the case wherein a rotational barrier is substantially high in energy that the population of molecules with a conformation outside the locked conformation is insignificant, such as in the hexasubstituted benzenes disclosed herein. Hexasubstituted benzene intermediates disclosed herein may exhibit such a locked conformation and preserve the locked conformation upon further reaction to incorporate various types of entities, such as those comprising a sensing functionality and/or other types of entities designed to promote sensing of an analyte of interest, as well as functional groups capable of functionally modifying a surface in a specified way.

When the hexasubstituted benzenes are functionalized in the manner disclosed herein, the locked conformation may dispose orthogonal reactive functionality toward opposing faces of the phenyl ring, with one group of reactive functionalities being capable of promoting covalent bonding to a surface and another group of reactive functionalities directed toward the opposite face of the phenyl ring, which may be further functionalized with entities suitable for promoting sensing of one or more analytes or for otherwise modifying the properties of a surface. The term "orthogonal" refers to the condition of two groups of reactive functionalities having different modes of reactivity, such that the two groups of reactive functionalities may be functionalized differently. The reactive functionalities directed away from the surface may become functionalized with various groups suitable for promoting modification of the surface in a desired way, such as through introducing hydrophobic modifications, hydrophilic modifications, molecular recognition sites, chromophores, fluorophores, luminescent groups, antimicrobial agents, tethered metal atoms or complexes, or the like. As such, once the hexasubstituted benzenes have become attached to a surface, the surface modifications may be directed outwardly from the surface in a conformationally controlled manner facilitated by the regular atomic arrangement afforded by the phenyl ring.

More specifically, each group of reactive functionalities is located upon alternating ring carbon atoms of the hexasubstituted benzenes of the present disclosure in order to accomplish the foregoing. Thus, three surface-reactive functionalities and three reactive functionalities (or sensing functionalities) may be present on alternating phenyl ring carbon atoms, with the reactive functionalities (or sensing functionalities) directed toward the opposite face of the phenyl ring and away from the surface. The hexasubstituted benzenes of the present disclosure are capable of tripodal covalent bonding to a surface, although fewer points of covalent bonding attachment may be possible in some cases. Similarly, up to three surface-modifying groups, such as functional groups designed to promote sensing of an analyte, may extend from the phenyl ring away from the surface.

Advantageously, various surface-reactive functionalities having high surface reactivity may be readily introduced in the hexasubstituted benzenes of the present disclosure in order to promote facile tripodal covalent bonding. When tripodal covalent bonding occurs to a surface, the phenyl ring may orient substantially parallel to the surface, thereby projecting the three functionalities directed toward the opposite face of the phenyl ring outwardly from the surface in an orientationally controlled manner. Even if no additional functionalization of these outwardly directed functionalities is conducted following surface attachment, some innate surface modification may be realized due to the hydrophobic nature of the phenyl ring itself. The outwardly directed functionalities further modifying the surface may be the same or different depending on particular application needs. In any event, a dense and regular arrangement of surface-modifying functionalities may be introduced according to the disclosure herein.

Particular variations of the hexasubstituted benzenes of the present disclosure, especially for sensing applications, may include those having a binding group, a reporter group and a buffer group attached and directed toward one face of the hexasubstituted benzene, and having multiple surface-reactive groups preattached and directed toward the opposite face of the hexasubstituted benzene. The buffer group may be present to stabilize the sensor output if a measurable quantity or binding affinity associated with the sensing functionality displays variance with pH. If a buffer group is not present or needed, a second binding group or a second reporter group may be present upon the hexasubstituted benzene, or a functional group that neither aids nor hinders binding or reporting may be present. Another variation may include attachment of a hexasubstituted benzene to a surface with protected functional groups attached to the hexasubstituted benzene and directed toward the face of the hexasubstituted benzene opposite the surface, in which case the protecting groups may be removed and the hexasubstituted benzene further functionalized while bound to the surface.

The present disclosure provides facile access to several hexasubstituted benzene intermediates that may serve as in-common synthons for introducing additional functionality thereto and further for bonding the hexasubstituted benzenes to a surface with a controlled orientation of the additional functionality. A wide range of additional functionality may be nucleophilically introduced onto the hexasubstituted benzenes while accomplishing the foregoing, thereby allowing synthesis of a wide range of hexasubstituted benzenes capable of modifying a surface or promoting analyte sensing. As discussed further hereinbelow, the orthogonal groups of reactive functionalities directed toward each face of the phenyl ring may be transformed in various alternative manners to expand the range of synthetic flexibility offered by the hexasubstituted benzenes described herein.

Other functionalities may be covalently bonded to the hexasubstituted benzenes of the present disclosure before or after the surface-reactive functionalities become covalently bonded to a surface. Choice of whether to covalently bond other functionalities to the hexasubstituted benzenes before or after surface functionalization takes place may depend upon whether the other functionalities interfere with the surface attachment chemistry or the coverage density. When the other functionalities are introduced after bonding of the hexasubstituted benzene to a surface, the hexasubstituted benzene may contain suitably protected functionalities that may be subsequently deprotected, possibly sequentially, and reacted to introduce the other functionalities while the hexasubstituted benzene is covalently bound to the surface. In either case, a wide range of functionalities may be introduced to a surface in a controlled orientation facilitated by the phenyl ring. In particular examples, suitable surface-reactive functionalities and other functionalities capable of further modifying a surface may be introduced nucleophilically to a hexasubstituted benzene in order to accomplish the foregoing, as described in further detail herein. Other techniques for surface attachment are also possible using the various hexasubstituted benzenes disclosed herein.

Advantageously, the present disclosure may facilitate the manufacture and testing of custom plates suitable for chemical analyses through automation and/or robotic manipulation afforded by the hexasubstituted benzenes disclosed herein. A sensor may be deposited as a finished sensor or as a protected intermediate. Suitable surfaces for covalent bonding of the hexasubstituted benzenes thereto are wide-ranging and may include, for example, acrylics, other plastics, glass, metals, ceramic, cement, wood, geological materials, and the like. The surface may contain suitable functionality for undergoing a chemical reaction to form a covalent bond with a complementary functional group in the hexasubstituted benzene. In non-limiting examples, a surface may bear an alkene that may undergo a free radical reaction with an alkene group in the hexasubstituted benzenes or an alkyne group that may undergo a cycloaddition reaction with an azide in the hexasubstituted benzenes. In another example, a surface may bear an electrophile for reaction with a benzylic amine in the hexasubstituted benzenes. Other functional groups may also be suitable for promoting covalent bond formation, as described in further detail hereinafter. In non-limiting examples, a protected intermediate may comprise a methacrylate functionality directed toward one face of the hexasubstituted benzenes with one or more amines protected and directed toward the other face. Alternately, the active portion of a finished sensor may be attached directly to a surface with a sensing functionality, a dye, and a buffer directed toward one face of the hexasubstituted benzenes and acrylic functionalities directed toward the opposite face for surface attachment. Heretofore, the art of preparing high efficiency chemical testing assays from premanufactured plates may take considerable time and skill, and the testing reagents may remain in solution during the analyses. Furthermore, the testing options available from premanufactured plates may be very expensive. Some of the hexasubstituted benzenes described herein may react readily with an appropriately functionalized surface, with little to no expertise being required to promote covalent bonding to the surface. Reaction and covalent bonding of the hexasubstituted benzenes with a surface may facilitate production of robust flow-through sensors as a non-limiting example, wherein the hexasubstituted benzene may carry functionality both for promoting covalent bonding and facilitating molecular association with an analyte of interest in a desired manner.

Once a sensor has been covalently attached to a surface at designated coordinates, such as in an array or similar ordered arrangement upon a surface, electronics may probe the surface at an appropriate spot through the use of electromagnetic radiation. The sensors may absorb (absorption spectroscopy) or emit (fluorescence spectroscopy) electromagnetic radiation or chemiluminescent as a result of a chemical reaction where the product is light. As such, the present disclosure may alleviate the limitation of solution-based testing when the reagents are part of the solution instead of attached to the surface, as may be facilitated with the hexasubstituted benzenes of the present disclosure. Alternately, electronics may be used to detect changes in electrical current or electrical potential for some types of sensors. In addition, the present disclosure may also allow for very precise use of small electronics to probe a surface at a designated location for sensing functionalities built on the hexasubstituted benzene platform.

Access to hexasubstituted benzene in-common synthons suitable for conducting further synthetic transformations thereon to introduce one or more functionalities for sensing or surface modification may be realized through a series of chemical reactions outlined in Scheme 1 below. The alternating facial disposition of the substituents upon the phenyl ring is denoted by bolded and dashed bonds in the structures below. It is to be understood that when any hexasubstituted benzene structure herein lacks bolded or dashed bonds, all possible diastereomers of the structure are implicitly described.

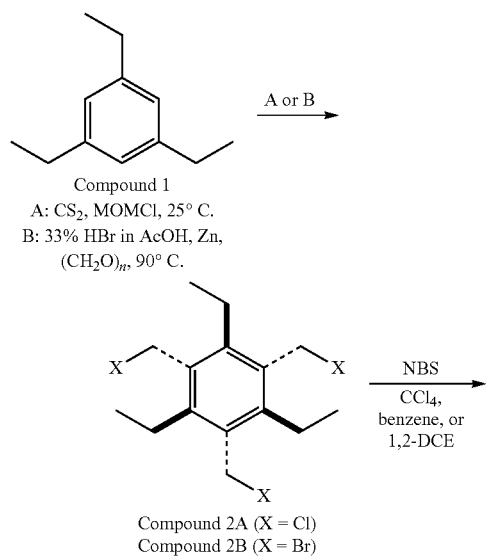

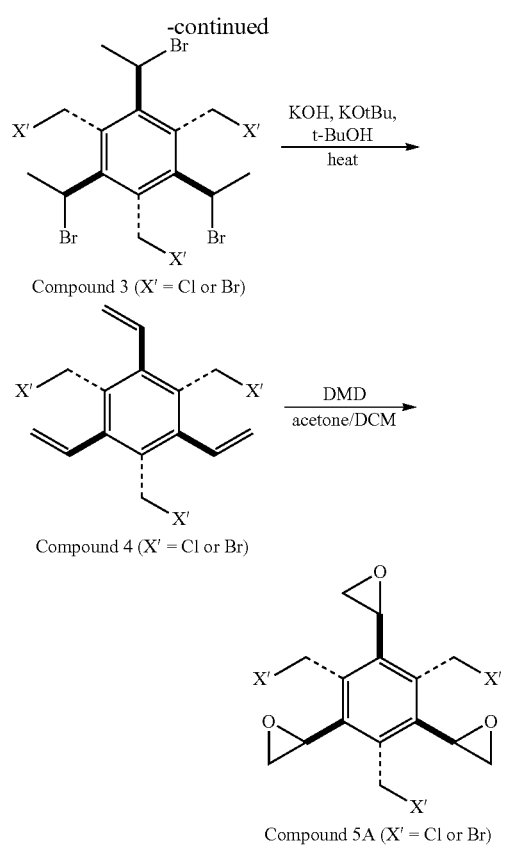

Referring to Scheme 1, 1,3,5-triethylbenzene (Compound 1) may be purchased commercially or synthesized by forming a thermodynamic Friedel-Crafts alkylation product. The remaining ring carbon atoms in Compound 1 may then be halomethylated using either chloromethyl methyl ether (MOMCl)/$CS_2$ (Conditions A) or HBr/Zn/paraformaldehyde (Conditions B) to afford either Compound 2A or 2B, as described in Wallace, et al., "Preparation of 1,3,5-Tris(aminomethyl)-2,4,6-triethylbenzene from Two Versatile 1,3,5-Tri(halosubstituted) 2,4,6-Triethylbenzene Derivatives," Synthesis, 2005, pp. 2080-2083. Compound 2A or Compound 2B may then be brominated at the α-position of the ethyl group using N-bromosuccinimide (NBS) to form Compound 3. If Compound 2A is brominated with NBS, some or all of the chlorides may exchange for bromides, particularly if a sufficient excess NBS is used. A mixture of benzylic halides in Compound 3 and in subsequent products, if formed, may be used satisfactorily to conduct the further synthetic transformations shown in Scheme 1 and in additional schemes discussed below. Alternately, elemental bromine may be used as the bromide source for conducting the bromination reaction. Other radical initiators, such as benzoyl peroxide, or electromagnetic radiation in the visible or ultraviolet region of the electromagnetic spectrum may also be used for initiating the bromination reaction, with the choice of electromagnetic radiation wavelength being chosen based upon the bromide source and the substrate undergoing bromination. Still other suitable bromination conditions may include those utilizing carbon tetrabromide, an electromagnetic radiation source, an absorption species, and/or a radical promoter. Morpholine and many tertiary amines may serve as a suitable radical promoter in this reaction.

Referring still to Scheme 1, the α-bromoethyl groups in Compound 3 may undergo dehydrobromination in the presence of a hindered tertiary amine, potassium t-butoxide or a similar base to form the corresponding vinyl groups in Compound 4. In some instances, a phase transfer catalyst, such as a crown ether or a tetraalkylammonium salt may be used to promote this reaction in an organic solvent such as dichloromethane, tetrahydrofuran or t-butanol. Finally, the vinyl groups of Compound 4 may be epoxidized using potassium peroxymonosulfate (OXONE), dimethyldioxirane (DMD), a peracid (e.g., MCPBA) or similar oxidants capable of selectively epoxidizing alkenes to afford Compound 5A. Compound 5A may serve as a versatile in-common synthon for accessing additional hexasubstituted benzenes disclosed herein. Other hexasubstituted benzene compounds shown in Scheme 1 may also constitute versatile synthons for promoting a reaction with a surface, as discussed further herein.

In some instances, incomplete dehydrobromination may occur in forming Compound 4, in which case a mixture comprising Compounds 4, 4A and 4B may be obtained, along with unreacted Compound 3, as shown in Scheme 1A.

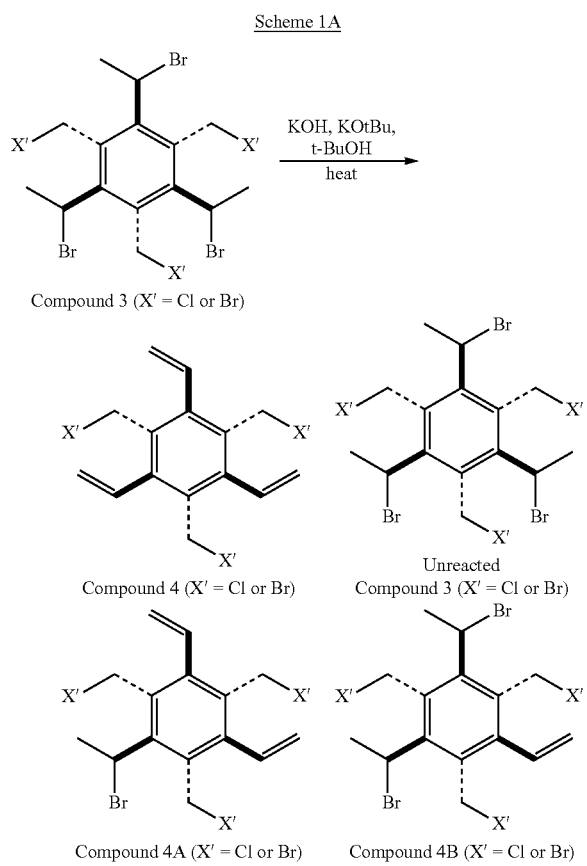

This mixture of compounds may still undergo epoxidation (for compounds containing vinyl groups), which may then afford further functionalized compounds containing one, two or three additional substituents prepared through epoxide ring opening, as discussed below. When starting with a mixture of this type, the functionalized products bearing different numbers and/or types of further substituents may be easily separable from one another.

Although benzylic halides are generally considered to be very good leaving groups, the benzylic halides in the hexasubstituted benzenes of the present disclosure are surprisingly low in reactivity with all but select nucleophiles. Without being bound by any theory or mechanism, it is believed that the particular orientation of the halomethyl groups with respect to the phenyl ring may limit their ability to undergo backside attack by many types of nucleophiles. Since the benzylic carbon is displaced from the plane of the phenyl ring, conjugation of a benzylic carbocation with the pi (π) bonds of the aromatic ring is also not possible. Similarly, the steric interactions around the ring are believed to force the vinyl groups to break conjugation with the pi (π) bonds of the aromatic ring. This permits an unexpected vinyl group stabilization to be realized compared with typical vinylbenzenes, such as styrene, which often polymerize readily under mild conditions. Although the benzylic halides are surprisingly low in reactivity, the low reactivity advantageously facilitates the synthetic transformations of the ethyl groups to form epoxides, as shown in Scheme 1 above.

Certain nucleophiles may undergo a facile reaction with the benzylic halides in the hexasubstituted benzenes disclosed herein. In particular, azide nucleophiles may undergo a high-yield reaction with the benzylic halides to form the corresponding benzylic azides. The benzylic azides may be further transformed to a benzylic amine, if desired, or undergo a direct dipolar cycloaddition reaction to form a 1,2,3-triazole that may facilitate use of the hexasubstituted benzenes in various applications. Functionalization of the benzylic amine or benzylic azide may promote attachment of the hexasubstituted benzenes to a surface, as discussed further hereinbelow. Alternately, surface attachment may be promoted through the vinyl groups, and the benzylic amines or benzylic halides may be further functionalized into groups tailored to suit a particular application.

Surprisingly, an azide nucleophile may react with the benzylic halides without promoting nucleophilic opening of the epoxides in particular hexasubstituted benzene compounds of the present disclosure. Specifically, as shown in Scheme 2 below, Compound 5A may be reacted with sodium azide to form Compound 5B, which bears intact epoxides in combination with the benzylic azides. Like Compound 5A, Compound 5B may also serve as a versatile in-common synthon for forming additional hexasubstituted benzenes disclosed herein, including hexasubstituted benzenes functionalized to promote detection of an analyte and/or suitable for attachment to an appropriate surface. Further details concerning introduction of the azide groups at a later synthetic stage and additional transformations of the azide groups are discussed in more detail below. Epoxidized variants of Compounds 4A and 4B may be reacted similarly to introduce three azide groups thereto.

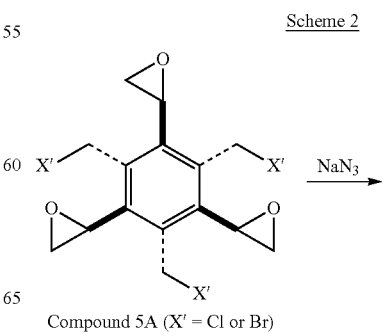

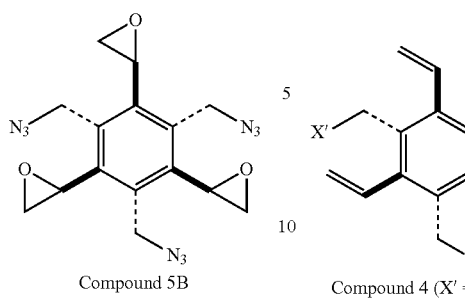

Compound 5B

In another example, Compound 3 may be transformed into Compound 3A, as shown in Scheme 2A, by reacting the secondary benzylic bromides with sodium azide.

Scheme 2A

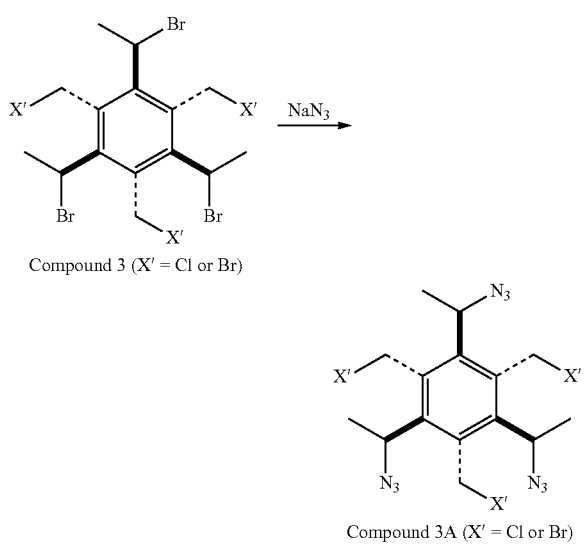

Without being bound by theory or mechanism, it is believed that the secondary benzylic halide may react faster with sodium azide than does the primary benzylic halide. Thus, chemoselectivity may be achieved, particularly when X' is Cl and the secondary benzylic halide is Br. Compound 3A is also a useful synthetic intermediate, which may undergo a similar sequence of reactions to those discussed below. As a non-limiting example, the secondary azide groups may undergo a reaction to promote surface attachment (e.g., through undergoing a cycloaddition reaction or reduction to form an amine group), and the primary benzylic halides may thereafter undergo nucleophilic displacement with azide to form primary benzylic azides that themselves may be further modified synthetically to introduce one or more sensing functionalities or related moieties. For example, the primary benzylic azides may be reduced to primary amines, which may then be alkylated or acylated in non-limiting examples to modify the properties of a surface or to introduce one or more functionalities capable of promoting sensing of an analyte of interest.

In still another example, Compound 4 may undergo hydrosilylation to introduce a trialkylsilyl group and form Compound 4C, as shown in Scheme 2B.

Scheme 2B

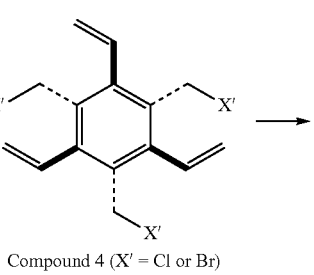

Compound 4 (X' = Cl or Br)

Compound 4C (X' = Cl or Br)

Compound 4C is also a useful synthetic intermediate, which may undergo a similar sequence of reactions to those discussed below. As a non-limiting example, the primary benzylic halides in Compound 4C may undergo nucleophilic displacement with azide to form primary benzylic azide groups, which may then undergo a further reaction to promote surface attachment in various ways.

In still another example, Compound 4 may undergo a reaction with azide to form the corresponding primary benzylic azides in Compound 4D, as shown in Scheme 2C.

Scheme 2C

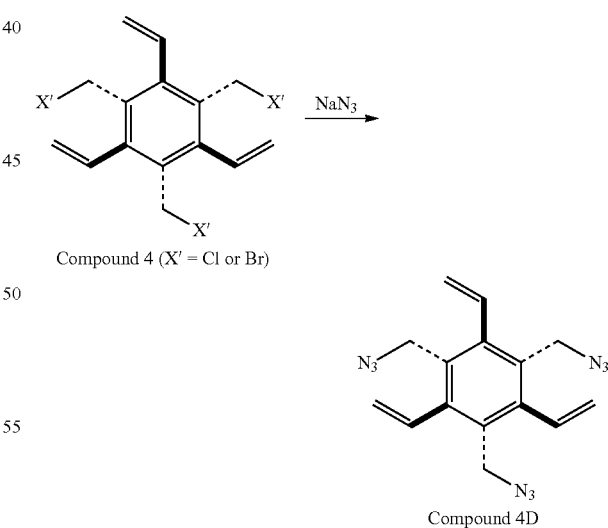

Compound 4D

The benzylic azides may then undergo a cycloaddition reaction to form a covalent bond to a surface, or the benzylic azides may undergo reduction to form benzylic amines, which may then be reacted to form a covalent bond to the surface. The vinyl group may project away from the surface and provide a handle for introducing one or more sensing functionalities or other groups capable of modifying a surface in a desired way. In one example, the vinyl groups may be epoxidized in order to introduce a sensing functionality or similar group through nucleophilic opening of the epoxides. In non-limiting examples, the vinyl groups may be oxidized to form a diol or primary alcohol or undergo oxidative cleavage to form a 1,3,5-substituted benzenetricarboxylic acid, any of which may be further functionalized to introduce a sensing functionality through covalent bond formation. In another synthetic approach, the vinyl groups may be reacted with an alkene to produce olefin dimers or higher oligomers.

In still another synthetic approach, the vinyl groups of Compound 4 may be reduced to the corresponding ethyl group, and azides may be introduced as in Scheme 2C. After subsequent reduction, the resulting amine groups may be utilized to introduce functionality suitable for promoting binding and/or analysis of an analyte of interest, particularly if binding of the hexasubstituted benzene to a surface need not take place.

Accordingly, various embodiments of the present disclosure provide hexasubstituted benzenes having a structure corresponding to Compound 6 below, Compound 6

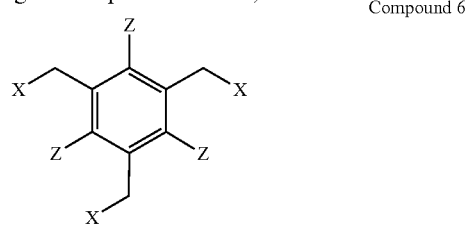

wherein each X is independently Cl, Br or $N_3$, and each Z is independently —CH(Br)CH$_3$, —CH($N_3$)CH$_3$, —CH=CH$_2$, —CH$_2$CH$_3$, —CH$_2$CH$_2$SiR$_3$, or epoxide, wherein R' is a hydrocarbyl group, such as a $C_1$-$C_{10}$ alkyl group. In more specific embodiments, each X is independently Cl, Br or $N_3$, and each Z is independently —CH(Br)CH$_3$, —CH=CH$_2$, or epoxide. Compound 6 may be a particular diastereomer, in which groups extending from alternating aromatic ring positions are directed toward opposing faces of the benzene ring.

In more particular embodiments, the hexasubstituted benzenes described herein may correspond to Compound 3, in which each Z is —CH(Br)CH$_3$ and each X is Br or each X is Cl. In other more particular embodiments, the hexasubstituted benzenes described herein may correspond to Compound 4, in which each Z is —CH=CH$_2$ and X is Br or each X is Cl. In still other more particular embodiments, the hexasubstituted benzenes described herein may correspond to Compound 5A, in which each Z is epoxide and each X is Br or each X is Cl. In yet still other more particular embodiments, the hexasubstituted benzenes described herein may correspond to Compound 5B, in which each Z is epoxide and each X is $N_3$. As referenced above, Compounds 5A and 5B may be particularly versatile in-common synthons for producing additional hexasubstituted benzenes disclosed herein, as described in further detail below.

Other particular examples of Compound 6 include those wherein each X and Z are selected as above, but each Z is not necessarily the same. Mixtures of such variants of Compound 6 are also encompassed by the disclosure herein. Illustrative mixtures may include those in which Z is a mixture of —CH(Br)CH$_3$ and —CH=CH$_2$, or —CH=CH$_2$ and epoxide.

As discussed above, Compounds 3-5A/B and similar hexasubstituted benzenes may bear two groups of orthogonal reactive functionality directed toward opposite faces of the phenyl ring at alternating ring carbon atoms. Therefore, Compounds 3-5A/B and similar hexasubstituted benzenes may exist as stereoisomers. Thus, in Compound 3, for example, the benzylic halides are directed toward one face of the phenyl ring and the α-bromoethyl groups are directed toward the opposite face of the phenyl ring. Similarly, in Compounds 5A and 5B, the benzylic halides or benzylic azides, respectively, are directed toward one face of the phenyl ring and the epoxide groups are directed toward the opposite face of the phenyl ring. The groups of orthogonal reactive functionality directed toward opposing faces of the phenyl ring may be exploited to introduce further functionality in an orientationally controlled manner, as discussed hereinafter.

Compound 5A has three epoxides directed toward one face of the phenyl ring and three benzylic halides directed toward the opposite face of the phenyl ring. Each group of reactive functionalities may be reacted separately to introduce further functionality to the hexasubstituted benzenes, as discussed further in reference to Scheme 3. As shown in Scheme 3 below, the epoxides in Compound 5A may be further reacted with one or more nucleophiles (Nu:) to promote epoxide ring opening without disturbing the benzylic halides, thereby forming Compound 7. Suitable nucleophiles may include nitrogen nucleophiles such Scheme 3

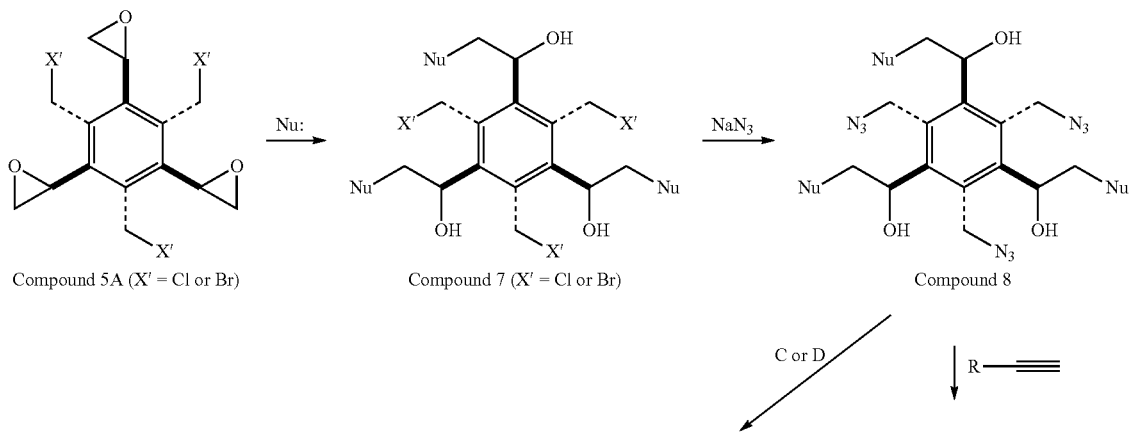

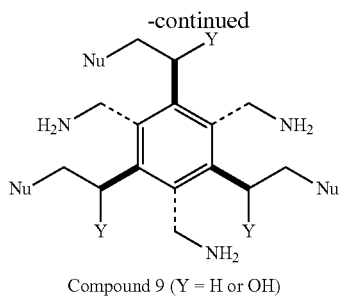

Compound 9 (Y = H or OH)

C = H₂, Pd/C, (Y = H)
D = PPh₃, (Y = OH)

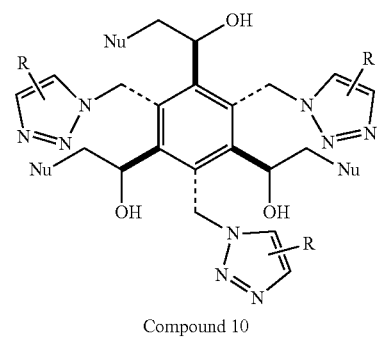

Compound 10 as primary or secondary amines. According to various embodiments of the present disclosure, the one or more nucleophiles may bear functionality configured to promote sensing of an analyte of interest or for modifying a surface in a desired way. Particular examples may include the one or more nucleophiles featuring a spectroscopically active entity, one or more nucleophiles featuring an entity capable of undergoing molecular association with an analyte of interest, and/or one or more nucleophiles capable of promoting a desired chemical environment to promote sensing, such as through providing a buffering moiety. After epoxide ring opening has taken place, the benzylic halides may then undergo a reaction with sodium azide to form the corresponding benzylic azides (Compound 8). The benzylic azides may then undergo reduction to an amine to form Compound 9 or undergo dipolar cycloaddition with an alkyne (R—C≡CH, R is a hydrocarbyl group, such as a $C_1$-$C_{10}$ alkyl group or any aryl group) to form Compound 10 to introduce further functionality onto the phenyl rings. The resulting 1,2,3-triazole in Compound 10 may promote bonding to a surface, as discussed in further detail below. Mono- or bis-epoxides, prepared by epoxidizing Compounds 4B or 4A, respectively, may undergo a similar series of reactions.

Referring still to Scheme 3, the nucleophile that promotes epoxide ring opening may become appended at the β-position with respect to the phenyl ring, thereby placing a hydroxyl group at the α-position, as shown in Compound 7. Without being bound by any theory or mechanism, the presence of the α-hydroxyl groups may enhance microenvironment solubility in proximity to the phenyl ring to promote enhanced binding once surface bound. The other regioisomer may form to a limited extent in some cases to introduce the hydroxyl group at the β-position and the nucleophile at the α-position. Although Scheme 3 has shown a single nucleophile opening each epoxide, it is to be recognized that multiple nucleophiles may be used, in which case statistical opening of the epoxides with the various nucleophiles may occur to form a range of products, provided that the multiple nucleophiles exhibit a comparable rate of reaction during epoxide ring opening. Thus, in some embodiments of the present disclosure, a first epoxide may be opened with a first nucleophile, a second epoxide may be opened with a second nucleophile, and a third epoxide may be opened with a third nucleophile, in which the first, second and third nucleophiles are all different. If formed and if needed, product mixtures may be separated by a suitable laboratory separation technique such as column chromatography, crystallization, or the like. Optionally, the α-hydroxyl group may be removed by reduction prior to displacing the benzylic halides (not shown in Scheme 3). Still other strategies may react the epoxides with orthogonally protected nucleophiles which may be deprotected at a later time for sequential attachment of functionalities suitable to promote sensing of a desired analyte. As a non-limiting example, two or more protected amines may comprise Nu: in Scheme 3 above (e.g., any combination of BOC, imide, FMOC or sulfonamide groups, as non-limiting examples), which may be individually deprotected and further functionalized to introduce functionalities suitable for sensing of modifying a surface in a desired manner.

Referring still further to Scheme 3, the benzylic azides in Compound 8 may be further manipulated to introduce additional functionality upon the hexasubstituted benzene (i.e., directed toward the face of the phenyl ring opposite the ring-opened epoxides). In some embodiments, the benzylic azides may be reduced to a benzylic amine to form Compound 9, such as through Staudinger reduction with triphenylphosphine or catalytically using hydrogen and a Pd/C catalyst. Catalytic reduction of the azides using hydrogen and Pd/C may concurrently reduce the α-hydroxyl group to form the corresponding methylene compound. Staudinger reduction, in contrast, may leave the α-hydroxyl group intact. In other embodiments, the azides may undergo a 1,3-dipolar cycloaddition reaction with a terminal alkyne to form the corresponding 1,2,3-triazole, as shown for Compound 10. The benzylic amine or the 1,2,3-triazole may be further exploited to promote surface attachment, as discussed further hereinbelow. Alternately, the benzylic amines may undergo a reaction to introduce a functionality capable of sensing or binding an analyte of interest. In addition or alternately, the α-hydroxyl groups may be further manipulated, such as under Mitsunobu conditions (triphenylphosphine, diethylazodicarboxylate (DEAD)) to introduce a nucleophile at the α-position, such as a carboxylic acid ester, an azide, an imide, an aryl ether, or a sulfonamide. Should removal of the α-hydroxyl groups be desired, the carboxylic acid ester may be reduced with a hydride reagent to affect removal.

Similar to the discussion for Compound 5A, Compound 5B has three epoxides directed toward one face of the phenyl ring and three benzylic azides directed toward the opposite face of the phenyl ring. Each group of reactive functionalities may be reacted separately to introduce further functionality to the hexasubstituted benzenes, as discussed in reference to Scheme 4 below.

Scheme 4

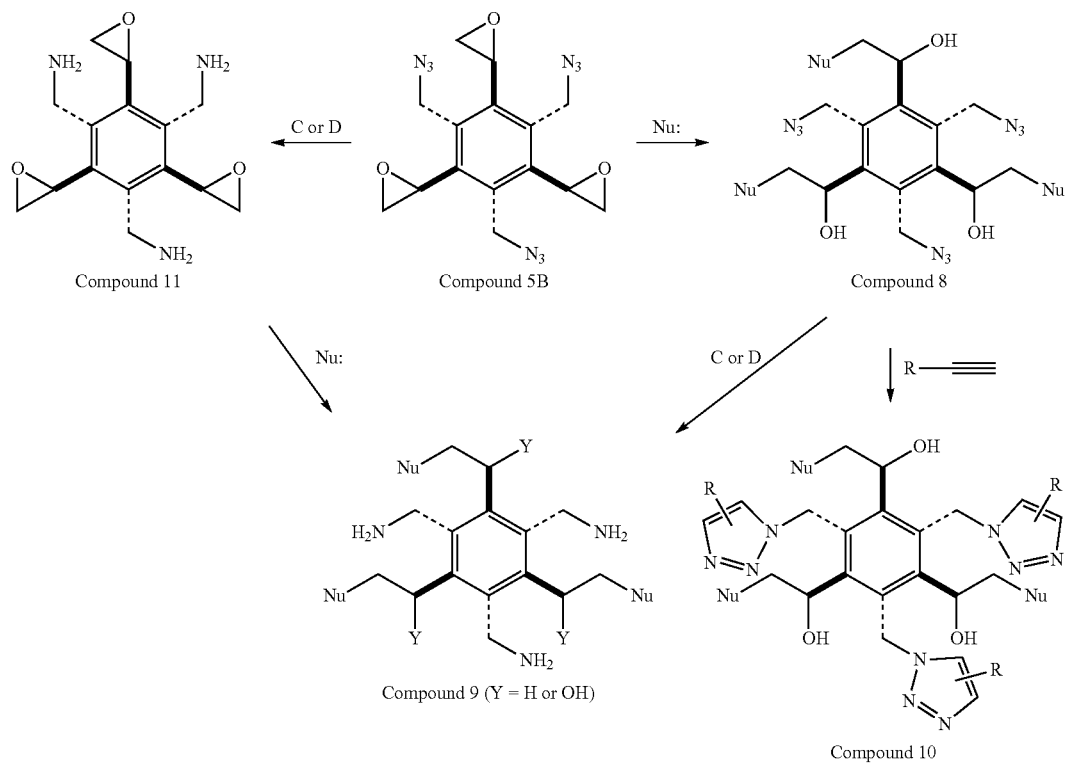

C = H₂, Pd/C
D = PPh₃

As shown in Scheme 4, the epoxide rings in Compound 5B may be opened with a nucleophile without disturbing the benzylic azides to form Compound 8, the same intermediate formed in Scheme 3 above. The benzylic azides of Compound 8, in turn, may be transformed in a similar manner to that described above in reference to Scheme 3 to form Compound 9 or Compound 10. Alternately, the benzylic azides may be reduced to the corresponding benzylic amines without disturbing the epoxides, thereby forming Compound 11. The epoxides in Compound 11, in turn, may then undergo nucleophilic opening to afford Compound 9, wherein the amine groups may be optionally further transformed into a functional group capable of promoting binding or analysis of an analyte of interest. Thus, depending on particular synthetic needs, the order of epoxide ring opening and benzylic halide displacement may be reversed. As with Scheme 3 above, a first epoxide in Scheme 4 may be opened with a first nucleophile, a second epoxide may be opened with a second nucleophile, and a third epoxide may be opened with a third nucleophile, in which the first, second and third nucleophiles are the same or all different. Product mixtures may be resolved by a suitable laboratory separation technique. Mono- or bis-epoxides, prepared by epoxidizing Compounds 4B or 4A, respectively, may undergo a similar series of reactions.

Accordingly, various embodiments of the present disclosure provide hexasubstituted benzenes having a structure of Compound 12 below,

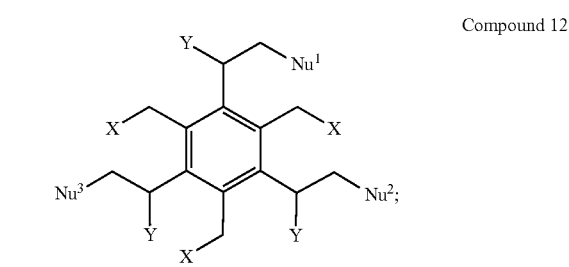

Compound 12 wherein $Nu^1$, $Nu^2$ and $Nu^3$ are each nucleophiles, each X is independently Cl, Br, $N_3$, $NH_2$, or NHQ, and each Y is independently H or OH. Q is an alkyl, aryl or polyether, optionally bound to the nitrogen atom via a carbonyl group. Q may bear further functionality for binding or interacting with an analyte of interest.

In more particular embodiments, $Nu^1$, $Nu^2$ and $Nu^3$ are each different. As used herein with respect to the nucleophiles, the term "different" refers to $Nu^1$, $Nu^2$ and $Nu^3$ differing structurally from one another, either compositionally or isomerically. $Nu^1$, $Nu^2$ and $Nu^3$ may each be of the same class of nucleophile or different. Illustrative classes of nucleophiles that may be suitable for use in epoxide ring opening according to the disclosure herein include, for example, nitrogen nucleophiles, such as primary or secondary amines. Phosphines, thiols, selenols, selenides, diselenides, alkoxides, carboxylates, and/or carbanions may also be suitable nucleophiles. In an illustrative embodiment, $Nu^1$, $Nu^2$ and $Nu^3$ may comprise orthogonally protected amines, such as amines protected with any combination of BOC, imide, FMOC or sulfonamide groups. For example, when $Nu^1$, $Nu^2$ and $Nu^3$ are amines orthogonally protected with BOC, phthalimide and a sulfonamide, respectively, the amine corresponding to $Nu^1$ may be exposed with dilute acid, the amine corresponding to $Nu^2$ may be exposed with dilute base, and amine corresponding to $Nu^3$ may carry a suitable sensing functionality upon the sulfonamide hydrocarbyl group. Other combinations of orthogonal protecting groups for amines may also be suitable, as can be appreciated by one having ordinary skill in the art. For instance, in another non-limiting example, $Nu^1$, $Nu^2$ and $Nu^3$ may be amines that are orthogonally protected with BOC, FMOC or phthalimide, or CBZ to allow the amines to be exposed through staged exposure to acid, base, and reducing conditions (e.g., catalytic hydrogenolysis), respectively. Such strategies may allow the amines to be sequentially exposed and reacted with a sensing functionality, a spectroscopically active functionality and/or a buffering functionality to promote sensing under various conditions. Sequential introduction of other types of functionalities may be realized similarly.

According to more particular embodiments, each X in Compound 12 may be Br or each X may be Cl. Alternately, each Br or Cl may be displaced with azide, such that each X in Compound 12 is $N_3$. In still other embodiments, each azide in Compound 12 may be reduced to form a benzylic amine, such that each X in Compound 12 is $NH_2$ and Y is either H or OH depending on how the reduction is performed, as discussed above. For example, catalytic reduction of the benzylic azide may reduce the benzylic alcohol to a methylene group, whereas triphenylphosphine reduction (Staudinger reduction) of the benzylic azide may leave the benzylic alcohol intact.

As referenced in brief above, the present disclosure also provides surface-bound reaction products of the hexasubstituted benzenes disclosed herein. Specifically, the group of reactive functionalities directed toward one face of the phenyl ring may undergo reaction with suitable functional groups upon a surface to result in up to tripodal covalent bonding of the hexasubstituted benzene to the surface. Less than tripodal covalent bonding of the hexasubstituted benzenes to a surface is also possible if not all of the reactive functionalities undergo a reaction. The remaining group of reactive functionalities directed toward the opposite face of the phenyl ring face, away from the surface, may be reacted to form other types of functional groups, as discussed above. For example, according to some embodiments, the reactive functionalities facing away from the surface may be reacted with one or more nucleophiles (e.g., nitrogen nucleophiles) to affix one or more desired functionalities upon the surface in a fixed orientation. Up to three functionalities may be directed toward one face of the phenyl ring located opposite the location of surface attachment. Advantageously, either of the groups of reactive functionalities in Compounds 5A or 5B may be suitably reacted with a surface to afford the surface-bound molecular scaffolds disclosed herein. The choice of which group of reactive functionalities to react with the surface may be dictated by the type of surface and the type of surface functionalities that are present. Illustrative approaches for forming such surface-bound hexasubstituted benzenes are discussed hereinafter.

Some embodiments of the present disclosure may include a reaction product of a hexasubstituted benzene that may be covalently bonded to a surface. The hexasubstituted benzene, before being covalently bonded to the surface, may have a structure corresponding to Compound 13

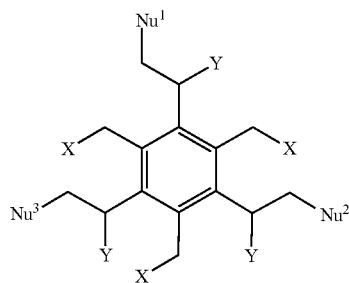

Compound 13 wherein $Nu^1$, $Nu^2$ and $Nu^3$ are each nucleophiles that may be the same or different, each X is Cl, Br, $N_3$ or $NH_2$, particularly each X is $N_3$ or $NH_2$, and each Y is independently H or OH. In forming a surface-bound hexasubstituted benzene, each $N_3$ or $NH_2$ may be reacted to form a linking group as a reaction product that is covalently bonded to a surface, as shown in Compound 14 below.

In some or other embodiments, surface-bound hexasubstituted benzenes disclosed herein may comprise a base surface, and a reaction product of the base surface and a hexasubstituted benzene covalently bonded to the surface, specifically a hexasubstituted benzene bearing an amine or an azide, in which the reaction product has a structure represented by Compound 14

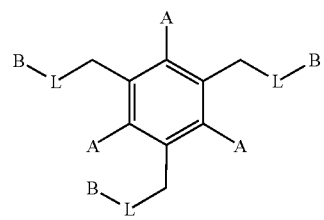

Compound 14 wherein B is a base surface, each A is a vinyl group, a reaction product of a vinyl group, an epoxide or a reaction product formed from opening of an epoxide with a nucleophile, and each L is a linking group connecting a benzylic carbon of the hexasubstituted benzene to the base surface. Each linking group L is formed from an azide or an amine bonded to the benzylic carbon, specifically a reaction product formed between a functionality upon the base surface and the azide or amine located upon the benzylic carbon. As such, each linking group L may comprise a reaction product of the azide or the amine, according to various embodiments of the present disclosure.

Base surfaces that may undergo covalent functionalization with the hexasubstituted benzenes disclosed herein are not considered to be particularly limited. In illustrative embodiments, suitable surfaces may be selected from a polymer surface, a metal surface, a ceramic surface, a glass surface, a cement surface, a wood surface, a geological surface (e.g., a rock or earthen surface), and any combination thereof. The type of base surface undergoing functionalization and the surface functional groups thereon may dictate the type of linking group that is chosen for covalently bonding the hexasubstituted benzene to the surface. Particular examples are discussed hereinafter. Particular examples of surface functionalization may include the use of materials suitable for being exposed to lateral flow when conducting analyses. This type of surface functionalization, regardless of the underlying base surface material (substrate), may depend upon antibody chemistry for selectivity. Hexasubstituted benzenes of the present disclosure are particularly suited for the preparation of lateral flow assays with high selectivity and geometric placement of chemistries upon a base surface to selectively detect and signal the presence of various analytes.

Suitable linking groups L formed from a benzylic azide may comprise a 1,2,3-triazole or similar cycloaddition reaction product of the benzylic azide. Such linking groups may be formed by reacting the benzylic azide with a surface-bound terminal alkyne in a dipolar cycloaddition reaction. Thus, according to some embodiments, modified surfaces of the present disclosure may have structures corresponding to Compounds 15 and 16 shown in Scheme 5 below. Although Scheme 5 has shown Compounds 15 and 16 being accessed via Compound 5B, it is to be appreciated that Compound 16 may be similarly accessed via Compound 5A (see Scheme 3). Surface-bound terminal alkynes may be directly appended to the base surface undergoing functionalization or be spaced apart therefrom by a grouping of one or more atoms connected to the base surface. Thus, 1,2,3-triazole linking groups need not necessarily exhibit direct bonding to the base surface in the manner depicted in Scheme 5. In illustrative embodiments, suitable surface-bound terminal alkynes may be present as a polymer side chain, or as appended surface functionalization upon a glass, metal, ceramic, concrete, wood, geological, or similar type of surface.

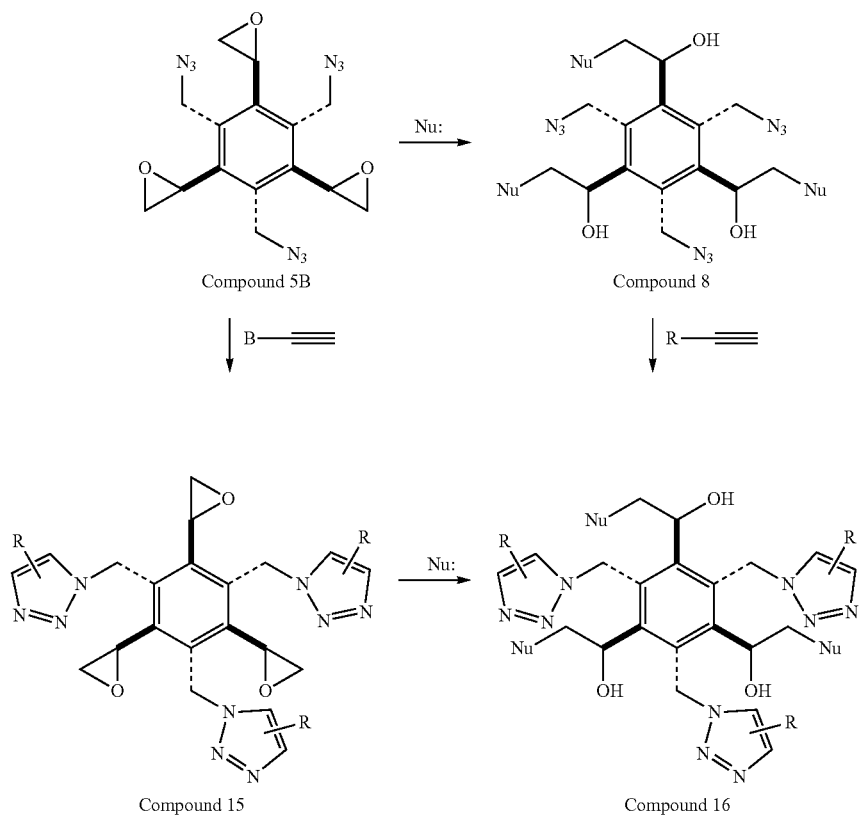

Scheme 5

Suitable linking groups L formed from a benzylic amine may incorporate the benzylic amine in a grouping of atoms extending between the benzylic carbon and a base surface undergoing covalent functionalization with the hexasubstituted benzenes. Such linking groups may be formed by reacting the benzylic amine with an amine-reactive functionality already covalently bonded to the base surface, or by first reacting the benzylic amine with a grouping of atoms containing further functionality that is reactive with one or more functional groups present upon the base surface and then reacting the functionalized benzylic amine with the base surface in a separate synthetic step. In either case, reaction of the benzylic amines to form linking groups may take place before or after epoxide opening, as shown in Schemes 6 and 7 below. Linking groups L formed from a primary benzylic amine may comprise a secondary or tertiary benzylic amine reaction product or a secondary or tertiary amide reaction product in non-limiting examples.

Scheme 6

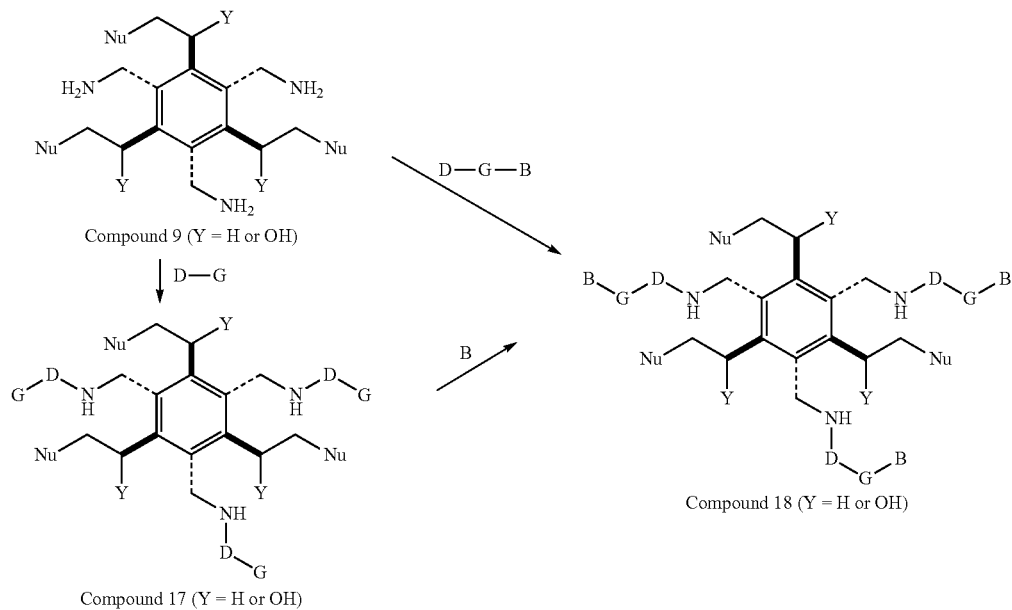

Scheme 7

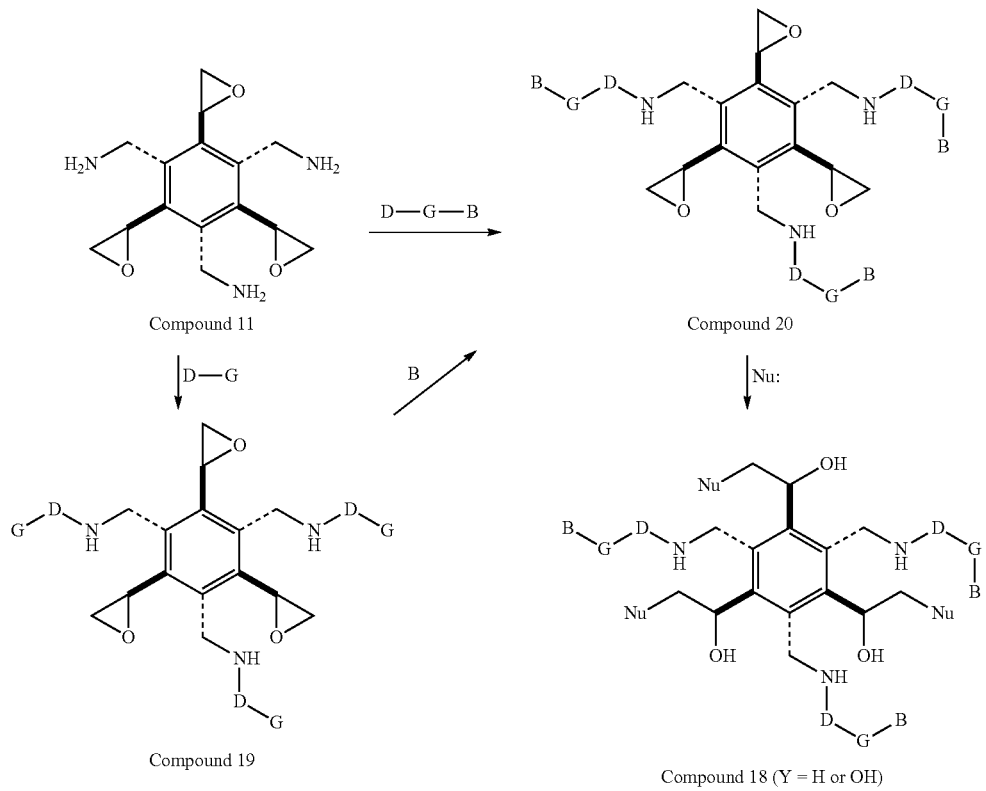

As shown in Scheme 6, the benzylic amines in Compound 9 may be reacted with an entity D-G, wherein D comprises a grouping of atoms reactive with the benzylic amine and G comprises a grouping of atoms that is reactive with base surface B, to form Compound 17. Compound 17, in turn, may then be reacted with base surface B to form Compound 18, in which the hexasubstituted benzene is covalently bonded to the surface. Compound 18 may be formed alternately by reacting a base surface pre-functionalized with entity D-G, such that entity D reacts with the benzylic amine to promote covalent bonding of the hexasubstituted benzene to the surface. Entity G may already be incorporated within base surface B, such that no separate synthetic step is necessary. Although Scheme 6 has shown a single nucleophile affecting epoxide ring opening, it is to be appreciated that a first nucleophile $Nu^1$ may open a first epoxide ring, a second nucleophile $Nu^2$ may open a second epoxide ring, and a third nucleophile $Nu^3$ may open a third epoxide ring, wherein at least one of $Nu^1$, $Nu^2$ and $Nu^3$ is different.

As an illustrative example, the grouping of atoms D in entity D-G may comprise an electrophile that is reactive with the benzylic amine. Suitable electrophiles that may react with the benzylic amine include, but are not limited to, leaving groups such as halides or sulfonates, acyl halides, Michael acceptors, epoxides, or the like. The electrophile may or may not remain intact within linking group L after reacting with the benzylic amine. Particularly suitable examples of linking group L may comprise secondary or tertiary benzylic amines or secondary or tertiary amides. The grouping of atoms G in entity D-G may be selected to react with one or more functional groups located upon base surface B. For example, in the case of a polymer surface, the grouping of atoms G may comprise a functional group that is reactive with a polymer side chain or is itself polymerizable when combined with other monomers under suitable conditions. In the case of a glass surface, grouping of atoms G may comprise a silane to form Si—O bonds with surface hydroxyl groups upon the glass surface.

As shown in Scheme 7, benzylic amines may also undergo single- or multi-step functionalization to promote surface attachment without disturbing the epoxides until a desired time. In particular, the benzylic amines in Compound 11 may be directly reacted with a suitably functionalized base surface to form Compound 20, in which entities D and G link base surface B to the benzylic carbon.

Alternately, the benzylic amines may be functionalized with entity D-G to introduce functionality that is reactive with the base surface (Compound 19), before forming Compound 20 in a subsequent synthetic step, wherein entity D-G is defined similarly to the corresponding entity D-G for Scheme 6. After covalently attaching the hexasubstituted benzene to the base surface, the surface-bound epoxides may then undergo opening with a suitable nucleophile to form Compound 18 to introduce a sensing functionality or other desired modification to the base surface, as discussed in further detail above. After opening of the epoxides with a suitable nucleophile, the resulting benzylic alcohols may either remain in the surface-bound reaction product (Y=OH) or undergo further reduction to affect their removal (R=H). Suitable techniques for removal of the benzylic alcohols are addressed in more detail above. Although Scheme 7 has shown a single nucleophile affecting epoxide ring opening, it is again to be appreciated that a first nucleophile $Nu^1$ may open a first epoxide ring, a second nucleophile $Nu^2$ may open a second epoxide ring, and a third nucleophile $Nu^3$ may open a third epoxide ring.

In a particular example, surface attachment may be realized by attachment of acrylic acid or a derivative thereof (e.g., acrylic acid, methacrylic acid, acrylamide, methacrylamide, and the like) to hexasubstituted benzenes following epoxide ring opening. In other particular instances, surface attachment may be realized by attachment of acrylic acid or a derivative thereof to the benzylic amines. In both instances, the vinyl group of the acrylic acid or acrylic acid derivative may be reacted thermally or optically through a free radical mechanism with a corresponding vinyl group on the surface, particularly a polymer surface bearing a free vinyl group or a vinyl-functionalized metal, glass, or ceramic surface. Scheme 8 below shows an illustrative process whereby an acrylate-functionalized hexasubstituted benzene may undergo attachment to a vinyl-functionalized surface.

Scheme 8

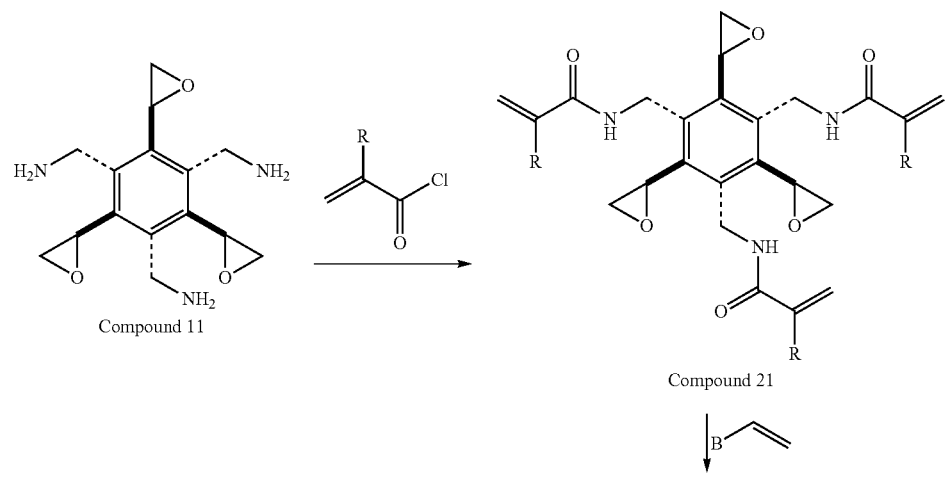

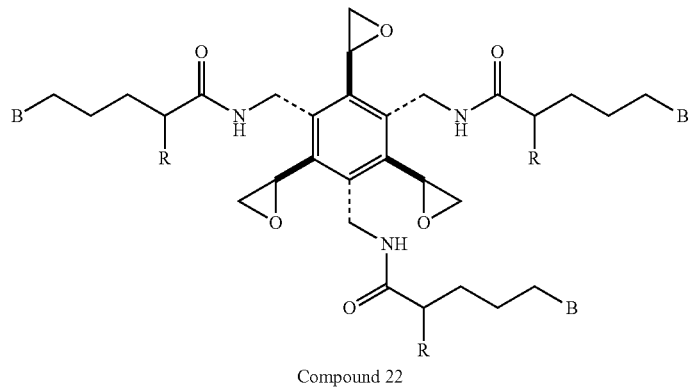

Compound 22

In Scheme 8, B represents a polymer surface or similar type of surface and R represents a hydrocarbyl group, particularly a methyl group. Once surface deposition and covalent bonding have taken place (Compound 22), the epoxide groups may be reacted to introduce functionalities suitable to promote sensing of a desired analyte or to modify a base surface in a desired manner.

In another synthetic alternative, a carboxylate form of acrylic or methacrylic acid may open the epoxides in Compound 11, and the amines may then undergo a reaction to introduce a functionality capable of binding or sensing an analyte of interest, as shown more generically in Scheme 9 below. Alternately, epoxide opening may take place at the azide stage prior to conversion of the azides into amines. The bound acrylic or methacrylic acid may then undergo polymerization with a reactive vinyl group to append the hexasubstituted benzene to a surface.

Another synthetic variant may be obtained by epoxidizing the product mixture in Scheme 1A and then reacting the various epoxides with methacrylic acid or a derivative thereof under basic conditions, such as in the presence of cesium carbonate, to promote nucleophilic epoxide opening. The resulting α-hydroxymethacrylate esters may then be reacted with an olefinic monomer or a surface olefin to promote surface attachment.

In view of the foregoing, particular examples of modified surfaces of the present disclosure may include those in which the hexasubstituted benzene has a structure represented by Compound 14A,

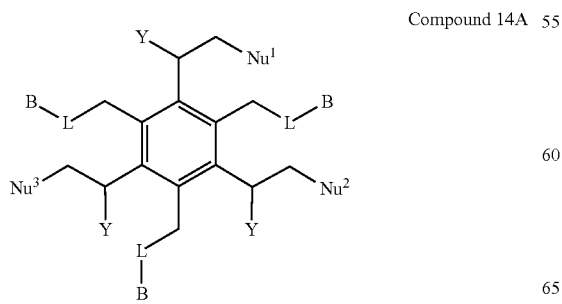

Compound 14A wherein $Nu^1$, $Nu^2$ and $Nu^3$ are each nucleophiles that may be the same or different, each Y is H or OH, and the other variables are defined as specified above.

The manner in which the hexasubstituted benzene becomes deposited upon a base surface in the course of becoming covalently bound thereto is not considered to be particularly limited. In some embodiments, the hexasubstituted benzene may be deposited by a technique such as inkjet printing, stencil printing or the like to result in thin-layer surface-bound patterns of the hexasubstituted benzenes having a defined shape. In other embodiments, spray coating or roller coating the hexasubstituted benzenes onto a surface bearing functionality suitable for promoting covalent bonding may be used to provide relatively uniform surface coverage. Other surface deposition techniques may also be suitable for use in the disclosure herein. In still other embodiments, the hexasubstituted benzenes may be combined under bulk reaction conditions with a compound bearing reactive functionality to promote covalent bonding between the two.

In the description above, covalent bonding of the hexasubstituted benzenes takes place through the benzylic carbon atoms and introduction of additional functionality takes place through nucleophilic opening of the epoxides. In alternative embodiments of the present disclosure, covalent bonding to a base surface may take place through the epoxides, and the benzylic carbon atoms may be employed for introducing further functionality. Such an approach is outlined in more detail in Scheme 9 below.

Scheme 9

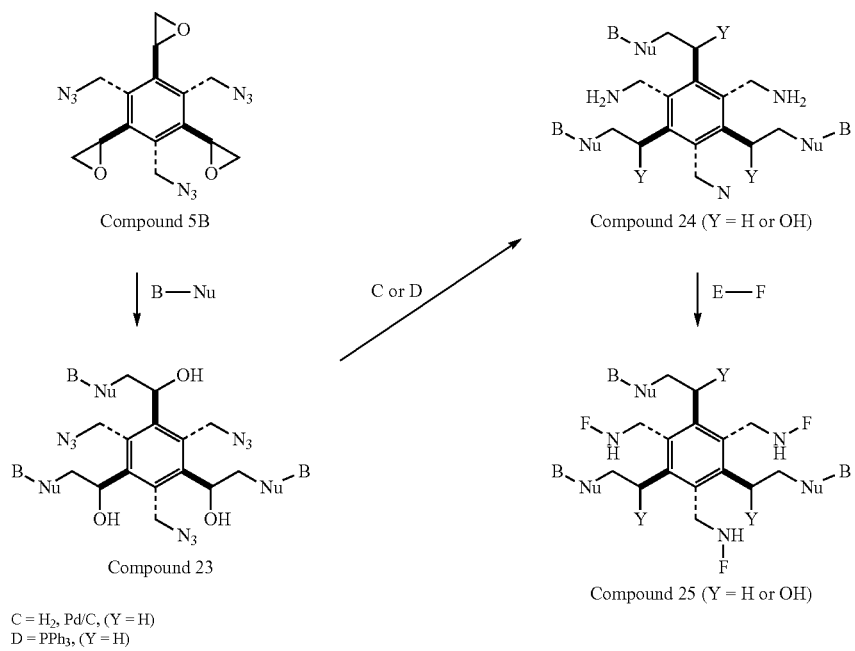

C = H₂, Pd/C, (Y = H)
D = PPh₃, (Y = H)

Referring to Scheme 9, the epoxides in Compound 5B may be reacted with a surface nucleophile to promote covalent attachment of the hexasubstituted benzene to a base surface, thereby forming Compound 23. Suitable surface nucleophiles may include, for example, primary or secondary amines or similar groups that are reactive with epoxides. Thereafter, the benzylic azides may be reduced, either catalytically with hydrogen and Pd/C or using triphenylphosphine (Staudinger reduction), thereby forming Compound 24. Depending on how the azide reduction is conducted, the benzylic hydroxyl group may either remain intact or undergo removal, as discussed above. After forming the benzylic amines in Compound 24, the benzylic amines may then undergo reaction with a grouping of atoms suitable to introduce additional functionality onto the benzylic amines, thereby forming Compound 25. Specifically, as shown in Scheme 9, grouping of atoms E-F may undergo a reaction with the benzylic amines, in which E is an electrophile and F is a functional group bonded to the electrophile. Suitable electrophiles may include, for example, leaving groups, acyl halides, Michael acceptors, epoxides and the like. The electrophile may remain bonded to the benzylic amine after undergoing a reaction therewith, or it may be displaced in the course of forming a linking group between the benzylic amine and functional group F. Functional group F may aid in promoting analysis of an analyte of interest or modifying a base surface in a desired manner.

As an alternative to the surface attachment procedure shown in Scheme 9, a benzylic halide such as Compound 5A may undergo surface attachment in a similar manner by reacting the epoxides with a surface nucleophile. Thereafter, the benzylic halides may be displaced with sodium azide, with the resulting benzylic azides being further functionalized in a manner similar to that discussed above in reference to Scheme 9.

As still another alternative to the surface attachment procedure shown in Scheme 9, the epoxides in Compound 5B may be nucleophilically opened with a reactive group, such as the carboxylate of acrylic or methacrylic acid. The azides may then be reduced to amines and undergo subsequent functionalization, as shown in Schemes 10 and 11 below. The bound acrylic or methacrylic acid may then undergo a reaction with a reactive alkene group to promote surface attachment. Compounds 25A and 25B show structures that may be capable of binding iron and lithium, respectively.

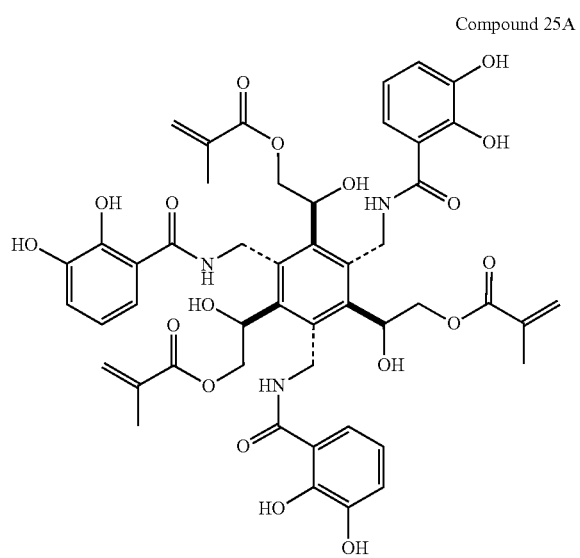

Compound 25A

-continued

Compound 25B

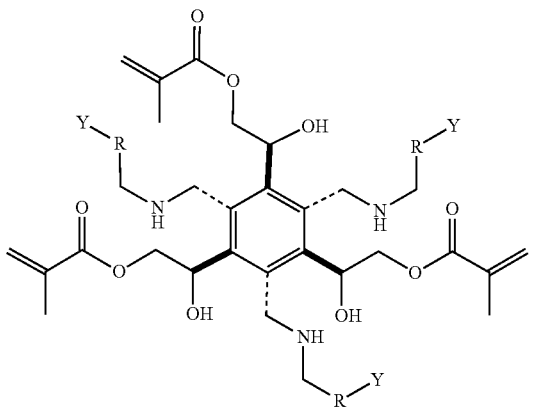

In Compound 25B, R is an alkyl, aryl or polyether, and Y is $CO_2H$, $P(=O)OH_2$, $SO_3H$, or $NHSO_2Z$, wherein Z is $CH_3$, $CF_3$, $C_6H_5$ or $C_6H_4NO_2$. In a particular example, R is $(CH_2)_n$ and Y is $CO_2H$, wherein n is an integer ranging from 2 to 4.

As illustrated above, the hexasubstituted benzenes disclosed herein are designed such that they may be reacted with one or more nucleophiles or other reactive compounds to introduce a range of further functionality directed toward a particular face of the hexasubstituted benzenes. In particular embodiments, the hexasubstituted benzenes may be reacted with a first nucleophile, a second nucleophile, and a third nucleophile that differ from one another to introduce three different moieties onto the hexasubstituted benzene. In other embodiments, the hexasubstituted benzenes may be reacted with a first nucleophile and a second nucleophile that differ from one another, such that the hexasubstituted benzenes incorporate two of one of the nucleophiles and one of the other nucleophile. The nucleophiles may all be the same in still other embodiments. Particularly suitable nucleophiles for use in the disclosure herein are nitrogen nucleophiles, wherein the nitrogen nucleophiles bear further functionality of interest for incorporation upon the hexasubstituted benzenes. In particular embodiments, one or more of the nucleophiles may bear functionality that undergoes a molecular association with an analyte of interest or modifies a base surface in a desired manner. The nucleophiles may bear hydrocarbyl groups of sufficient lengths to hydrophobically modify a surface and/or incorporate one or more heteroatom groups to hydrophilically modify the surface. In non-limiting examples, an amine-containing polyether may be reacted with the hexasubstituted benzenes in order to hydrophilically modify the surface. Other suitable groups that may be incorporated within the nucleophiles that react with the hexasubstituted benzenes may be envisioned by one having ordinary skill in the art and having the benefit of the disclosure herein. Other of the nucleophiles may be spectroscopically active to promote detection of molecular association with a binding group, and optionally one of the nucleophiles may comprise a buffering functionality to promote a desired pH range at which the molecular association of interest occurs.

In a specific example, hexasubstituted benzenes of the present disclosure may be covalently bonded to a polymer surface comprising a macroparticulate formed from glycidyl (meth)acrylate or a similar monomer bearing an epoxide side chain, followed by nucleophilic opening thereof. Such macroparticulates and use thereof are described in further detail in International Patent Applications PCT/US2020/041407 and PCT/US2020/041417, each filed on Jul. 9, 2020 and incorporated herein by reference in its entirety.

Suitable macroparticulates may comprise a reaction product of an epoxide-containing (meth)acrylic polymer or copolymer and a compound bearing a nitrogen nucleophile, which may open at least a portion of the epoxide groups in the polymer and form covalent bonds. The nitrogen nucleophile may be present upon the hexasubstituted benzene, or the hexasubstituted benzene may be introduced after nucleophilic epoxide opening has taken place. In addition, the functionalized (meth)acrylic polymers and copolymers may be further crosslinked to convey additional mechanical stability to the macroparticulates disclosed herein. Crosslinking may take place before or after reaction with the nitrogen nucleophile occurs.

Glycidyl methacrylate and similar monomers bearing a side-chain epoxide group may be polymerized and rendered into a form suitable for undergoing further functionalization. In particular, glycidyl methacrylate and similar monomers may be polymerized to a first polymerization state (e.g., through a living polymerization reaction or a free radical polymerization reaction) comprising a solid polymer product that may be isolated and rendered into a predetermined shape suitable for undergoing further functionalization, such as in the form of a sphere or extrudate. Other polymerization techniques (e.g., free radical polymerization, solution polymerization, suspension polymerization, or emulsion polymerization) may also be suitable to achieve the first polymerization state. The structure obtained after rendering the polymer into a desired shape in the first polymerization state is solid, although some minor voids may be present depending on manufacturing or processing inconsistencies. The density obtained after rendering the polymer into the predetermined shape may represent that of the as-obtained polymer from the polymerization reaction. A profile of the predetermined shape rendered at the pre-functionalization stage may be largely maintained following functionalization, except for undergoing volume expansion and a corresponding decrease in the density. That is, functionalization may promote an increase in size and/or other morphological changes of the pre-functionalization shape to afford the increased size and decreased density, while still maintaining the overall appearance of the predetermined shape following functionalization. An internal cavity may form during functionalization and particularly decrease the density. The internal cavity tends to be spherical or substantially spherical and differs from minor voids present in the pre-functionalization shape.

Suitable living polymerization conditions for (meth) acrylic monomers may include Cu(I) mediation in the presence of a suitable radical initiator, such as AIBN. It is also to be appreciated that suitable Cu(I) active species may be produced in situ by oxidation or reduction of Cu(0) or Cu(II), respectively. If left unquenched, the dangling reactive intermediate may undergo further polymerization when exposed to more olefinic monomer or another entity suitable for reacting with the reactive intermediate. In living-polymerized poly(glycidyl methacrylate) and similar (meth)acrylic polymers or copolymers, the dangling reactive intermediate may undergo further polymerization when functionalizing the polymer initially obtained in a first polymerization state (pre-functionalization), thereby affording a second polymerization state after functionalization with a nitrogen nucleophile has taken place. In the first polymerization state, the polymer may still be easily manipulated into a desired, predetermined shape, and then undergo further curing in conjunction with functionalization with a nitrogen nucleophile according to the disclosure herein. The second polymerization state may represent a higher molecular weight than does that of the first polymerization state.

When poly(glycidyl methacrylate) or a similar polymer is reacted with a nitrogen nucleophile in the presence of a suitable base, the polymer and its rendered shape may undergo a morphological change during functionalization. In particular, the shape rendered to the polymer or copolymer in the first polymerization state may undergo expansion, such that the shape is less dense and has a larger volume following functionalization with the nitrogen nucleophile. Spherical pre-functionalization shapes, for example, may form a hollow sphere upon functionalization with a nitrogen nucleophile. Other pre-functionalization shapes may similarly form an internal cavity upon functionalization, albeit with a more randomized exterior shape. Functionalization may occur (via epoxide opening with the nitrogen nucleophile) without the base being present, but volume expansion and internal cavity formation may not occur. Suitable bases for forming expanded macroparticulates may include a tertiary amine base, such as trimethylamine, triethylamine, N,N-diisopropylethylamine (Hünig's base), 2,2,6,6-tetramethylpiperidine, 1,8-diazabicyclo[5.4.0]undec-7-ene (DBU), 1,5-diazabicyclo[4.3.0]non-5-ene (DBN), 4-dimethylaminopyridine (DMAP) and the like. Other mild Lewis bases may also be suitable.

A suitably substituted hexasubstituted benzene may promote epoxide opening in accordance with the disclosure above. Alternately, a different nitrogen nucleophile may promote epoxide opening, and the hexasubstituted benzene may thereafter react with a reaction product formed during epoxide ring opening. Examples of nucleophiles that may be utilized in this manner include, for instance, ethylenediamine and iminodiacetic acid. Other aminopolycarboxylic acids, such as glutamic acid diacetic acid, methylglycine diacetic acid, or the like may also be suitable ligands for use in functionalizing the macroparticulates according to the disclosure herein. Similarly, other $C_2$-$C_8$ alkylenediamines, such as 1,3-propanediamine, 1,4-butanediamine, 1,5-pentanediamine, and 1,6-hexanediamine, may also be suitable for functionalizing the (meth)acrylic polymers and copolymers according to the disclosure herein, wherein further functionalization of the alkylenediamine may take place after the reaction with the macroparticulates takes place. Polyamines, including branched polyamines, may also be reacted with the macroparticulates and then further functionalized after a reaction with the macroparticulates takes place.

Macroparticulates produced according to the disclosure herein may be formed from a pre-functionalization, extruded shape having a diameter of about 1.5 mm to about 2.5 mm, typically about 2.25 mm. Spherical post-functionalization shapes formed from such extrudates (after rolling in a pre-functionalization spherical shape) may have an effective diameter ranging from about 5.5 mm to about 11 mm, or about 6.2 mm to about 8.6 mm, or about 6.2 mm to about 10.5 mm, or about 6 mm to about 6.5 mm, or about 6.5 mm to about 7.0 mm, or about 7.0 mm to about 7.5 mm, or about 7.5 mm to about 8.0 mm, or about 8.0 mm to about 8.5 mm, or about 8.5 mm to about 9.0 mm, or about 9.0 mm to about 9.5 mm, or about 9.5 mm to about 10.0 mm, or about 10.0 mm to about 10.5 mm, or about 10.5 mm to about 11.0 mm. Depending on shape, non-spherical shapes may have effective diameters (cross-sectional dimensions) ranging from about 5.0 mm to about 11.5 mm, or about 5.0 mm to about 6.0 mm, or about 6.0 mm to about 7.0 mm, or about 7.0 mm to about 8.0 mm, or about 8.0 mm to about 9.0 mm, or about 9.0 mm to about 10.0 mm, or about 10.0 mm to about 11.0 mm.

The hexasubstituted benzenes of the present disclosure may be utilized in various sensing applications when functionalized with moieties capable of undergoing a molecular association with a particular analyte of interest. Surface bound hexasubstituted benzenes capable of undergoing a molecular association with an analyte of interest may comprise at least a portion of a sensor. Additional electronics may produce a quantifiable signal in the presence of an analyte of interest, or the hexasubstituted benzenes may be spectroscopically interrogated in the presence of an analyte of interest to afford a response that may be correlated with the amount of analyte present. The moieties capable of undergoing molecular association with an analyte of interest may be introduced to the hexasubstituted benzenes by one or more nucleophiles that react with the epoxides, or if the epoxides are used for promoting surface attachment (Scheme 9), via other reactive functionalities such as electrophiles that are reactive with benzylic amines.

When used in sensing applications, the surface-bound hexasubstituted benzenes may be present in any suitable location for interacting with an analyte of interest. Illustrative locations may include, for example, an electrode, test strip, a flow cell (flow sensor), a static cell, or single-well surface configured to interact with a fluid containing an analyte of interest. In other instances, the surface-bound hexasubstituted benzenes may be incorporated upon a surface in individual wells of a multi-well plate, thereby facilitating parallel, high-throughput analyte analyses. When incorporated in a multi-well plate, each well may incorporate the same surface-bound hexasubstituted benzene (if multiple samples of the same analyte are to be analyzed in each well) or different surface-bound hexasubstituted benzenes in at least some of the wells (if different analytes are to be analyzed in certain wells).

Accordingly, sensors of the present disclosure may comprise a modified surface comprising a surface-bound hexasubstituted benzene, such as the hexasubstituted benzene defined by Compound 18. In particular embodiments, more than one type of nucleophile may be incorporated in the hexasubstituted benzenes, such that at least one of the nucleophiles includes functionality that may associate with an analyte of interest, and an extent of the association between the analyte of interest and the surface-bound hexasubstituted benzene is analytically detectable (e.g., spectroscopically or electrochemically) and correlatable to an amount of the analyte of interest that is present. More specifically, the hexasubstituted benzene may be reacted with $Nu^1$, $Nu^2$ and $Nu^3$, wherein at least one of $Nu^1$, $Nu^2$ and $Nu^3$ includes functionality that associates with an analyte of interest, the association is analytically detectable, and an extent of the association is correlatable to an amount of the analyte of interest that is present in a sample. For example, the sensor response may be referenced against a calibration curve or lookup table associated with the analyte being assayed with a particular hexasubstituted benzene. A single sensor having such sensing capabilities may be used in assaying one or more analytes in a complex fluid, or multiple sensors may be employed to assay multiple analytes.

Moieties capable of undergoing a molecular association with a particular analyte of interest are not considered to be especially limited. Suitable moieties may include entities such as chelating ligands, crown ethers, cryptands, porphyrins, calixarenes, analyte-sensitive dyes, pH sensitive compounds, antibodies, enzymes, proteins, biological receptors, or similar entities capable of undergoing a specific molecular interaction with an analyte of interest or a class of related analytes. Choice of a specific entity may be based upon the analyte of interest to be detected. Coordinative association of an analyte with a ligand may be desirable in some instances and facilitated by at least one of $Nu^1$, $Nu^2$ and $Nu^3$.

Analysis of the molecular association between the analyte of interest and the hexasubstituted benzene may be determined by any suitable analytical technique. In illustrative embodiments, suitable analytical techniques may include spectrophotometry or electrochemical detection techniques, as well as any combination thereof. The magnitude of the analytical response (e.g., signal intensity) may be correlated to a known amount of analyte using a lookup table, calibration curve or function, or the like.

In addition to a functionality capable of undergoing a specific molecular association with an analyte of interest (binder group), the surface-bound hexasubstituted benzenes may further include a functionality that allows the molecular interaction to be detected more readily. Specifically, a second nucleophile may introduce a functionality configured to promote spectroscopic or electrochemical detection of the hexasubstituted benzene (reporter group). The spectroscopic or electrochemical signature of such a functionality may change when an analyte of interest is associated with the hexasubstituted benzene compared to when the analyte is not associated.

The surface-bound hexasubstituted benzenes may also include an additional functionality that may increase or decrease the strength of the molecular association with the analyte of interest. For example, such functionalities may carry a pH buffer that may increase or decrease the strength of molecular association of pH-sensitive analytes. In other embodiments, such functionalities may carry moieties that may scavenge reactive species that may otherwise preclude formation of a molecular association with an analyte of interest. Other choices for the additional functionality may increase or decrease the electron density upon the phenyl ring to increase or decrease the strength of the molecular association with an analyte of interest as needed.

Accordingly, in some embodiments, the hexasubstituted benzenes may comprise three different functionalities introduced by nucleophiles to promote sensing of one or more analytes under appropriate conditions. In particular embodiments, at least one of the first nucleophile, the second nucleophile and the third nucleophile may carry functionality that is capable of associating with an analyte of interest in order to promote sensing thereof. In some or other embodiments, at least one of the first nucleophile, the second nucleophile and the third nucleophile may carry functionality that aids in promoting detection of the analyte of interest, specifically molecular association of the analyte of interest with the hexasubstituted benzene. In still additional embodiments, at least one of the first nucleophile, the second nucleophile, and the third nucleophile may carry functionality that changes the strength of the molecular association of the analyte of interest with the hexasubstituted benzene. In more specific embodiments, at least one of the first nucleophile, the second nucleophile, and the third nucleophile may serve as a buffer to prevent sensing from being triggered by an environmental change in pH or a similar event. Alternately, a buffer may facilitate a desired molecular association with an analyte of interest within a specific pH range.

Thus, in some embodiments, sensors of the present disclosure may comprise a surface-bound hexasubstituted benzene having three different functionalities introduced by nucleophiles to aid in promoting detection of an analyte of interest. A first functionality may undergo molecular association with the analyte of interest, a second functionality may promote detection of the molecular association, and the third functionality may include one or more moieties that alter the strength of the molecular association. Alternative hexasubstituted benzene configurations include those in which: 1) the first functionality is present in combination with two third functionalities or two first functionalities are present in combination with a third functionality, 2) the first functionality is present in combination with two second functionalities or two first functionalities are present in combination with a second functionality, or 3) three occurrences of the first functionality are present upon the hexasubstituted benzene. The alternative hexasubstituted benzene configurations may be used if the molecular association of the analyte of interest may be satisfactorily detected without introducing further functionality to the hexasubstituted benzenes.

For example, in particular embodiments of the present disclosure, the hexasubstituted benzenes may feature a first nucleophile carrying functionality capable of undergoing molecular association with an analyte of interest, and a second nucleophile carrying functionality that demonstrates a different spectroscopic, electrochemical, or electromechanical response when an analyte is bonded to or associated with the functionality carried by the first nucleophile. Moreover, the hexasubstituted benzenes may feature a third nucleophile carrying functionality that may further tailor the bonding or association of the analyte with the first nucleophile or alter the detection signature provided by the second nucleophile.

Illustrative analytes or classes of analytes that may undergo detection according to the disclosure herein are not considered to be particularly limited and include substances such as, for example, trace metals, salts, organics, poisons, biomarkers, metabolites, hormones, cells, toxins, drugs, nerve agents and other chemical warfare agents, explosives, microorganisms (including bacteria, viruses, protozoa, fungi, and the like), and the like. These and similar analytes may be analyzed in a diverse range of fields including, for example, process and system monitoring, water and other environmental analyses, health and safety, medical and diagnostic testing, oilfield testing and servicing, agricultural testing, industrial testing, and the like. Fluids that may be analyzed using the hexasubstituted benzenes disclosed herein include, for example, industrial waste water, process water, ground water, produced or flowback water from a wellbore, etching or digestion water from electronics processing, waste water streams, water from precious metal refining, water from catalyst waste refining, mining runoff water, geothermal brines, organic liquids, oil, blood, urine, other bodily fluids, and similar complex fluids. Other suitable analytes and fluids containing the analytes may be envisioned by one having ordinary skill in the art.

The hexasubstituted benzene compounds disclosed herein may be used to analyze and/or collect an analyte or other substance of interest from a fluid or from a surface, as discussed in more detail above. In alternative examples, the hexasubstituted benzene compounds of the present disclosure, including surface-bound variants thereof, may be preloaded with a substance and then released into a desired location, such as into a process stream. That is, the hexasubstituted benzene compound may function as a vehicle for conveying the substance to a desired location, wherein the substance may be removed by a stronger binding entity or through encountering less favorable binding conditions. The substance carried by the hexasubstituted benzene compound may be employed to treat or convey a change of various types at the location where the substance is released. Successful delivery of the preloaded substance may be verified by a spectroscopic or electrochemical change in the hexasubstituted benzene compound once the substance has been released therefrom. Accordingly, the present disclosure also provides hexasubstituted benzene compounds with a substance bound thereto, wherein the substance may be released under suitable conditions. Methods for using the hexasubstituted benzene compounds as a delivery vehicle may comprise: providing a hexasubstituted benzene compound with a substance bound thereto, exposing the hexasubstituted benzene compound to conditions that promote release of the substance, and optionally, assaying release of the substance by spectroscopically or electrochemically interrogating the hexasubstituted benzene compound. Any of the hexasubstituted benzene compounds disclosed herein may be employed for this purpose, including those covalently bonded to a surface.

The type of surface attachment of the hexasubstituted benzenes in sensors and sensing applications is not considered to be particularly limited. In accordance with the disclosure above, particular types of surface attachment may include a cycloaddition product of a benzylic azide, or a secondary or tertiary benzylic amine reaction product or a secondary or tertiary benzylic amide reaction product of a primary benzylic amine.

Accordingly, methods for forming modified surfaces and sensors comprising a surface modified with a hexasubstituted benzene may comprise: providing a base surface having a plurality of functionalities reactive with an amine or an azide; contacting the base surface with a hexasubstituted benzene having a structure represented by Compound 26

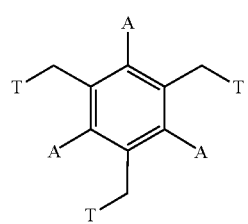

Compound 26 wherein each A is a vinyl group, a reaction product formed from a vinyl group, an epoxide, or a reaction product formed from opening of an epoxide with a nucleophile, and each T is independently, $N_3$ or $NH_2$; and reacting at least a portion of the plurality of functionalities with T to form a modified surface comprising a reaction product covalently bonded to the base surface an having a structure represented by Compound 14

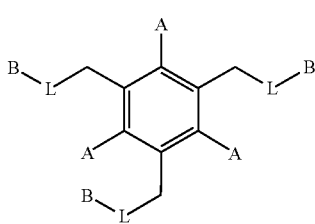

Compound 14 wherein B is the base surface, and each L is a linking group connecting a benzylic carbon of the hexasubstituted benzene to the base surface, each L being formed from a reaction between a functionality and T. In particular examples, the hexasubstituted benzene may have a structure represented by Compound 27

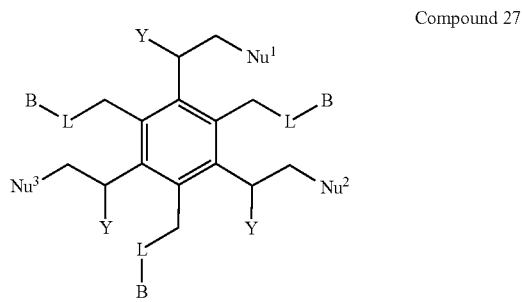

Compound 27 wherein $Nu^1$, $Nu^2$, and $Nu^3$ are nucleophiles, and each Y is independently H or OH, and L and B are specified as above. $Nu^1$, $Nu^2$, and $Nu^3$ may be the same or different and are specified in more detail above.

In summary, hexasubstituted benzenes of the present disclosure may create a targeted platform having a selected or pre-organized structure for binding with controlled orientation for purposes of detecting, identifying, and quantifying desired analytes with specificity. The hexasubstituted benzenes may function as a surface modifying agent, creating a detectable construct in the presence of the desired analyte. The hexasubstituted benzenes may function in this manner when contacting solid, liquid or gaseous phases. Solid surface modifications may also include modifying the innate properties of the surface, such as conveying antimicrobial, optical, specific binding properties (e.g., sulfur), or the like to a surface. In addition, the hexasubstituted benzenes disclosed herein may be attached to a first solid surface for contacting a second solid surface for purposes of detection. In a non-limiting example, a sensor comprising the hexasusubstituted benzenes may be fabricated on a cotton swab that is used for swabbing another surface for detection of various analytes thereon.

Hexasubstituted benzenes of the present disclosure may afford sensing capabilities by promoting interaction with an analyte of interest opposite the surface. Illustrative sensor embodiments may include: 1) hexasubstituted benzenes and completed sensors fabricated therefrom which comprise a binding group, a reporter dye for detecting a molecular interaction of interest, and a buffer, and which may be directly attached to a surface, particularly a surface bearing an acrylate functionality; or 2) hexasubstituted benzenes and completed sensors fabricated therefrom which comprise a binding group, a reporter dye for detecting a molecular interaction of interest, and a buffer, and which may be directly attached to a surface via a pendant azide functional group, particularly via a 1,3-dipolar cycloaddition reaction (oftentimes referred to as a Huisgen 'click reaction') between the azide functional group and an alkyne, more particularly a proparygylic acrylate derivative.

Hexasubstituted benzenes disclosed herein may feature bifacial reactivity having an azide functionality directed toward one face of the phenyl ring for promoting a 'click reaction' to a surface and an orthogonally reactive opposite face comprising a secondary benzylic azide, a secondary benzylic amine, a vinyl group, an epoxide group, or a protected amine. Other hexasubstituted benzenes featuring bifacial reactivity may feature an acrylate group directed toward one face of the phenyl ring for promoting an acrylate-type reaction with a suitably functionalized surface (e.g., by free radical bond formation) and an orthogonally reactive opposite face comprising a secondary benzylic azide, a secondary benzylic amine, a vinyl group, an epoxide group, or a protected amine.

In addition, the hexasubstituted benzenes disclosed herein may allow the optical properties of a surface to be altered in order to provide fluorescence, phosphorescence, or non-linear optical effects such as emission of polarized light from the surface.

In summary, hexasubstituted benzenes and associated sensor constructs may facilitate analyses of a wide range of fluids and analytes contained therein. The hexasubstituted benzenes may be robustly attached to the surface of a sensor construct in a highly orientationally controlled manner to accomplish the foregoing. Robust, orientationally controlled covalent bonding of a hexasubstituted benzene to a surface to promote analyte detection may overcome non-covalent detection approaches in which solutions of testing reagents are applied to a testing well or plate just prior to use. Such reagent loading appropriates are not feasible for flow-through sensing approaches with the testing reagent remaining unbound. Covalent attachment of a hexasubstituted benzene to a surface may particularly facilitate development of flow-through sensors for high-throughput, in-line analyses of various types of process streams.

Moreover, the present disclosure provides a versatile chemical system engineered to function as a sensor when analyzing both simple and complex fluids. In a simple example, the present disclosure may allow one to detect the chemical identity of the constituents in common drinking water. More broadly, any number of liquids used in commercial, industrial, or medical applications may be analyzed using this technology. In specific examples, a fluid may be a liquid that may contain solids, other liquids or gases in water, or any combination thereof. Other types of complex fluids may also be compatible with the sensing technology described herein. The present disclosure may be applied in a wide range of ways to promote reaction-based detection of a desired chemical in a fluid and produce a measurable result. Beneficially, the chemical system described herein may generate measurement data for a specific target even when a fluid contains many other elements that would confuse or block other common sensor systems. As nonlimiting examples, measurements can be made using the present disclosure in complex fluids that include naturally occurring or industrial process fluids such as oilfield water, radioactive water, or geothermal brines; biological fluids such as blood; food items and the like. The chemical system of the present disclosure may probe a surface without a "traditional" fluid being present, thereby providing measurement data to detect and quantify if an environmental surface has been exposed to specific toxins, bacteria, drugs, explosives, chemical weapons, poisons, or other elements of concern. As discussed herein, the chemical system has been engineered to feature a common scaffold with a design that includes a two-sided, or bifacial, features. The opposing faces of the hexasubstituted benzene compounds disclosed herein may have different reaction profiles that are used in different combinations to provide various types of sensing functionalities. The different reaction profiles have simplified the ability to permanently attach the scaffold to a range of surfaces, such as glass, metal, or plastic, while at the same time allowing the opposite side of the hexasubstituted benzene compound to specifically target and sequester particular chemical and biological targets of interest. In some cases, the hexasubstituted benzene compound can act as a chemical sensor that generates a measurable physical quantity from changes to optical or electrical signals when a chemical or biological target is acquired, thereby providing a measurement value of the target. In another non-liming example, the hexasubstituted benzene compound can be preloaded with a captured element prior to use, such that the scaffold can deploy the preloaded element when in the presence of a specified chemical target. That is, the hexasubstituted benzene compounds may be employed as a delivery system as well. The hexasubstituted benzene compounds disclosed herein may be particularly useful for creating reactive surfaces during 3D printing, chemical coatings, material additives, quantitative chemical measurements, selective capture and removal of targets from a fluid, such as water remediation, and use as real-time, flow-through measurement sensors. Thus, the present disclosure thus provides the basis of a system applicable to a variety of pressing problems in many industries including, for example, food processing, medical devices, medical testing, oilfield fluid remediation, oilfield fluid analytical testing, 3D printing, microbiological screening, chemical coatings, industrial process optimizations, additives, and environmental remediation efforts.

Embodiments disclosed herein include:

A. Hexasubstituted benzenes. The hexasubstituted benzenes have a structure of

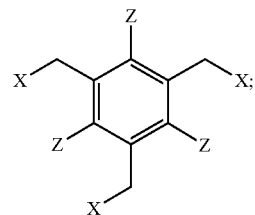

wherein each X is independently Cl, Br or $N_3$, and each Z is the same and independently —$CH(Br)CH_3$, —$CH(N_3)CH_3$, —$CH=CH_2$, —$CH_2CH_2SiR'_3$

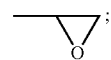

or wherein R' is a hydrocarbyl group.

B. Nucleophile-functionalized hexasubstituted benzenes. The hexasubstituted benzenes have a structure of

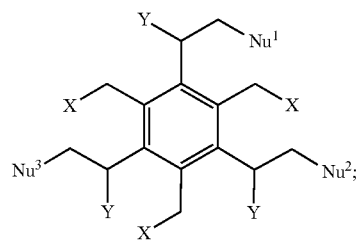

wherein $Nu^1$, $Nu^2$ and $Nu^3$ are each nucleophiles, each X is independently Cl, Br, $N_3$ or $NH_2$, and each Y is independently H or OH.

C. Surface-bound molecular scaffolds. The surface-bound molecular scaffolds comprise: a reaction product of a hexasubstituted benzene covalently bonded to a surface, the hexasubstituted benzene having a structure of

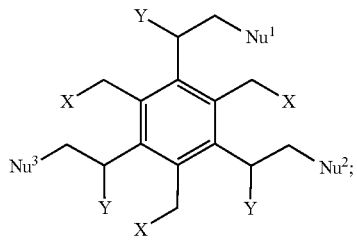

wherein $Nu^1$, $Nu^2$ and $Nu^3$ are each nucleophiles, each X is $N_3$ or $NH_2$, and each Y is independently H or OH; wherein each $N_3$ or $NH_2$ has been reacted to form a linking group that is covalently bonded to the surface.

D. Surface-bound molecular scaffolds. The surface-bound molecular scaffolds comprise: a surface; and a hexasubstituted benzene covalently bonded to the surface, the hexasubstituted benzene having a structure of

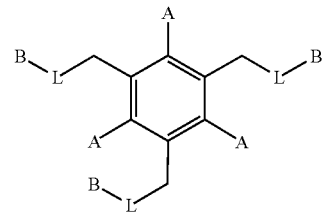

wherein each A is an epoxide or a reaction product formed from opening of an epoxide with a nucleophile; and wherein each L is a linking group connecting a benzylic carbon of the hexasubstituted benzene to the surface, each L being formed from an azide or an amine bonded to the benzylic carbon; wherein B is the surface.

E. Sensors comprising a surface-bound molecular scaffold. The sensors comprise a molecular scaffold comprising a surface; and a hexasubstituted benzene covalently bonded to the surface, the hexasubstituted benzene having a structure of

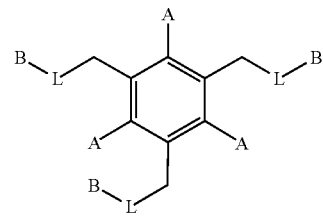

wherein each A is an epoxide or a reaction product formed from opening of an epoxide with a nucleophile; and wherein each L is a linking group connecting a benzylic carbon of the hexasubstituted benzene to the surface, each L being formed from an azide or an amine bonded to the benzylic carbon; wherein B is the surface; and wherein at least one of $Nu^1$, $Nu^2$ and $Nu^3$ includes functionality that associates with an analyte of interest; wherein an extent of the association between the analyte of interest and the surface-bound molecular scaffold is analytically detectable and correlatable to an amount of the analyte of interest.

Each of embodiments A-E may have one or more of the following additional elements in any combination:

Element 1: wherein each Z is —CH(Br)CH$_3$ and each X is Br or each X is Cl.

Element 1A: wherein each Z is independently —CH(Br)CH$_3$, CH=CH$_2$, or

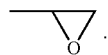

Element 2: wherein each Z is —CH=CH$_2$ and each X is Br or each X is Cl.

Element 3: wherein each Z is

and each X is Br or each X is Cl.

Element 4: wherein each Z is

and each X is $N_3$.

Element 5: wherein each X is Br or each X is Cl.

Element 6: wherein $Nu^1$, $Nu^2$ and $Nu^3$ are each different.

Element 6A: wherein $Nu^1$, $Nu^2$ and $Nu^3$ are each orthogonally protected amines.

Element 7: wherein each X is $N_3$.

Element 8: wherein each Y is OH.

Element 9: wherein each X is $NH_2$.

Element 10: wherein the surface is selected from the group consisting of a polymer surface, a metal surface, a ceramic surface, a glass surface, and any combination thereof.

Element 11: wherein each A has a structure of —CH$_2$(Y)CH$_2$(Nu); wherein Y is H or OH, and Nu is the nucleophile.

Element 12: wherein Y is OH and a first nucleophile $Nu^1$ reacts with a first epoxide, a second nucleophile $Nu^2$ reacts with a second epoxide, and a third nucleophile $Nu^3$ reacts with a third epoxide; wherein $Nu^1$, $Nu^2$ and $Nu^3$ are each different.

Element 13: wherein each L is a 1,2,3-triazole formed from a benzylic azide.

Element 14: wherein each L comprises a secondary amine.

Element 15: wherein at least one of $Nu^1$, $Nu^2$ and $Nu^3$ includes functionality that is spectroscopically or electrochemically active to promote detection of the analyte of interest.

By way of non-limiting example, exemplary combinations applicable to B include: 5 and 6 or 6A, or 6 or 6A and 7. Exemplary combinations applicable to D include 10 and 11; 10 and 12; 10 and 13; 10 and 14; 11 and 12; 11 and 13; 11 and 14; 12 and 13; and 12 and 14. Exemplary combinations applicable to E include 10 and 15; 11 and 15; 12 and 15; 13 and 15; 14 and 15; 10 and 11, optionally in combination with 15; 10 and 12, optionally in combination with 15; 10 and 13, optionally in combination with 15; 10 and 14, optionally in combination with 15; 11 and 12, optionally in combination with 15; 11 and 13, optionally in combination with 15; 11 and 14, optionally in combination with 15; 12 and 13, optionally in combination with 15; and 12 and 14, optionally in combination with 15.

Additional embodiments disclosed herein include:

A'. Hexasubstituted benzenes having a structure of

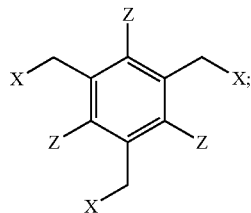

wherein each X is independently Cl, Br or $N_3$, and each Z is independently —$CH(Br)CH_3$, —$CH(N_3)CH_3$, —$CH=CH_2$, —$CH_2CH_3$,

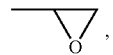

or, —$CH_2CH_2SiR'_3$;
wherein R' is a hydrocarbyl group.

B'. Hexasubstituted benzenes having a structure of

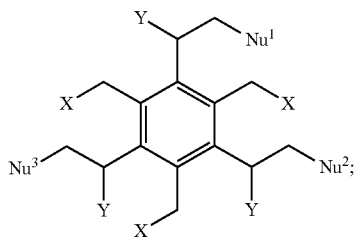

wherein $Nu^1$, $Nu^2$ and $Nu^3$ are each nucleophiles, each X is independently Cl, Br, $N_3$ or $NH_2$, and each Y is independently H or OH.

C'. Surfaces modified with a hexasubstituted benzene. The modified surfaces comprise: a base surface having a plurality of functionalities reactive with an amine or an azide; and a reaction product of the base surface and a hexasubstituted benzene bearing an amine or an azide, the reaction product being covalently bonded to the base surface and having a structure of

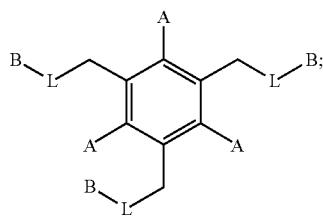

wherein B is the base surface; wherein each A is a vinyl group, a reaction product of a vinyl group, an epoxide, or a reaction product formed from opening of an epoxide with a nucleophile; and wherein each L is a linking group connecting a benzylic carbon of the hexasubstituted benzene to the base surface, each L being formed from a reaction between a functionality and an azide or an amine located upon the benzylic carbon.

D'. Sensors comprising a surface modified with the hexasubstituted benzene of C, wherein at least one of $Nu^1$, $Nu^2$ and $Nu^3$ includes functionality that associates with an analyte of interest; wherein association between the analyte of interest and the functionality of at least one of $Nu^1$, $Nu^2$ and $Nu^3$ is analytically detectable and an extent of the association is correlatable to an amount of the analyte of interest that is present in a sample.

E'. Methods for functionalizing a surface with a hexasubstituted benzene. The methods comprise: providing a base surface having a plurality of functionalities reactive with an amine or an azide; contacting the base surface with a hexasubstituted benzene having a structure of

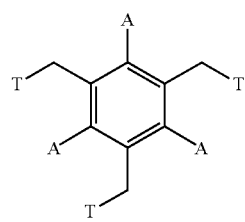

wherein each A is a vinyl group, a reaction product formed from a vinyl group, an epoxide, or a reaction product formed from opening of an epoxide with a nucleophile; and wherein each T is independently $N_3$ or $NH_2$; and reacting at least a portion of the plurality of functionalities with T to form a modified surface comprising a reaction product covalently bonded to the base surface and having a structure of

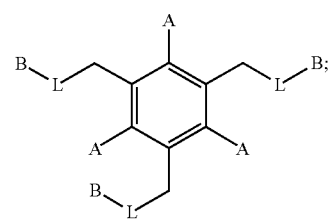

wherein B is the base surface; and wherein each L is a linking group connecting a benzylic carbon of the hexasubstituted benzene to the base surface, each L being formed from a reaction between a functionality and T.

Each of embodiments A'-E' may have one or more of the following additional elements in any combination:

Element 1': wherein each Z is independently —$CH(Br)CH_3$, —$CH=CH_2$, or

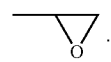

Element 2': wherein each Z is —$CH(Br)CH_3$ and each X is Br or each X is Cl.

Element 3': wherein each Z is —$CH=CH_2$ and each X is Br or each X is Cl.

Element 4': wherein each Z is —CH=CH$_2$ and each X is N$_3$.

Element 5': wherein each Z is

and each X is Br or each X is Cl.

Element 6': wherein each Z is

and each X is N$_3$.

Element 7': wherein each X is Br or each X is Cl.
Element 8': wherein each X is N$_3$.
Element 9': wherein each X is NH$_2$.
Element 10': wherein Nu$^1$, Nu$^2$ and Nu$^3$ are each different.
Element 11': wherein Nu$^1$, Nu$^2$ and Nu$^3$ are orthogonally protected amines.
Element 12': wherein each Y is OH.
Element 13': wherein L comprises a cycloaddition reaction product of a benzylic azide.
Element 14': wherein the cycloaddition reaction product is a 1,2,3-triazole.
Element 15': wherein L comprises a secondary or tertiary benzylic amine reaction product or a secondary or tertiary benzylic amide reaction product of a primary benzylic amine.
Element 16': wherein each A is an epoxide or a reaction product formed from opening of an epoxide with a nucleophile.
Element 17': wherein each A has a structure of —CH(Y)CH$_2$(Nu); wherein Y is H or OH, and Nu is the nucleophile.
Element 18': wherein a first nucleophile Nu$^1$ reacts with a first epoxide, a second nucleophile Nu$^2$ reacts with a second epoxide, and a third nucleophile Nu$^3$ reacts with a third epoxide.
Element 19': wherein the reaction product has a structure of

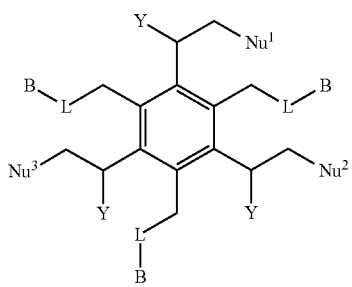

wherein Nu$^1$, Nu$^2$ and Nu$^3$ are each nucleophiles, and each Y is independently H or OH.

Element 20': wherein the base surface is selected from the group consisting of a polymer surface, a metal surface, a ceramic surface, a glass surface, a cement surface, a wood surface, a geological surface, and any combination thereof.

Element 21': wherein the association is coordinative with a ligand present upon the hexasubstituted benzene.

Element 22': wherein at least one of Nu$^1$, Nu$^2$ and Nu$^3$ includes functionality that is spectroscopically or electrochemically active to promote detection of the analyte of interest.

Element 23': wherein each A is an epoxide or a reaction product formed from opening of an epoxide with a nucleophile.

Element 24': wherein each A has a structure of —CH(Y)CH$_2$(Nu); wherein Y is H or OH, and Nu is the nucleophile.

Element 25': wherein the hexasubstituted benzene has a structure of

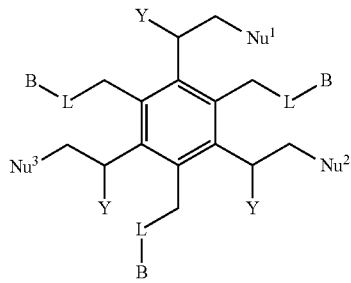

wherein Nu$^1$, Nu$^2$ and Nu$^3$ are each nucleophiles, and each Y is independently H or OH.

By way of non-limiting example, exemplary combinations applicable to B' include, but are not limited to: 7', 8' or 9', and 10'; 7', 8' or 9', and 11'; 7', 8' or 9', and 12'; 10' and 11'; and 10' and 12'. Exemplary combinations applicable to C' include, but are not limited to: 13' and 14'; 13', 14' and 16'; 15' and 16'; 15' and 17'; 13' and 18'; 13', 18' and 19'; 13', 18', 19' and 12'; 15', 18', and 19'; 15', 18', 19' and 12'; 13' and 20'; 15' and 20'; 10' and 13'; and 10' and 15'. Exemplary combinations applicable to D' include, but are not limited to: 21' and 22'; 22' and 24'; 22' and 13'; 22' and 15'; 24' and 13'; and 24' and 15'. Exemplary combinations applicable to E' include, but are not limited to: 20' and 23'; 20' and 24'; 20' and 25'; 25' and 10'; 25' and 11'; 20' and 13'; 20' and 15'; 23' and 13'; 24' and 13'; 23' and 15' and 24' and 15.

To facilitate a better understanding of the disclosure herein, the following examples of various representative embodiments are given. In no way should the following examples be read to limit, or to define, the scope of the invention.

Examples

Compound A: 1,3,5-Tris(chloromethyl)-2,4,6-triethylbenzene. The title compound was synthesized as described in K. J. Wallace, et al., "Preparation of 1,3,5-Tris(aminomethyl)-2,4,6-triethylbenzene from Two Versatile 1,3,5-Tri (halosubstituted) 2,4,6-Triethylbenzene Derivatives," Synthesis, 2005, pp. 2080-2083. In particular, 1,3,5-triethylbenzene was reacted with chloromethyl methyl ether in CS$_2$ in the presence of SnCl$_4$ to afford the title compound. CAUTION: chloromethyl methyl ether is a potent carcinogen.

Compound B: 1,3,5-Tris(bromomethyl)-2,4,6-triethylbenzene. The title compound was synthesized as described in K. J. Wallace, et al., "Preparation of 1,3,5-Tris(aminomethyl)-2,4,6-triethylbenzene from Two Versatile 1,3,5-Tri (halosubstituted) 2,4,6-Triethylbenzene Derivatives," Synthesis, 2005, pp. 2080-2083. In particular, 1,3,5-triethylbenzene was reacted with HBr, acetic acid and Zn powder to afford the title compound.

Figure 2:
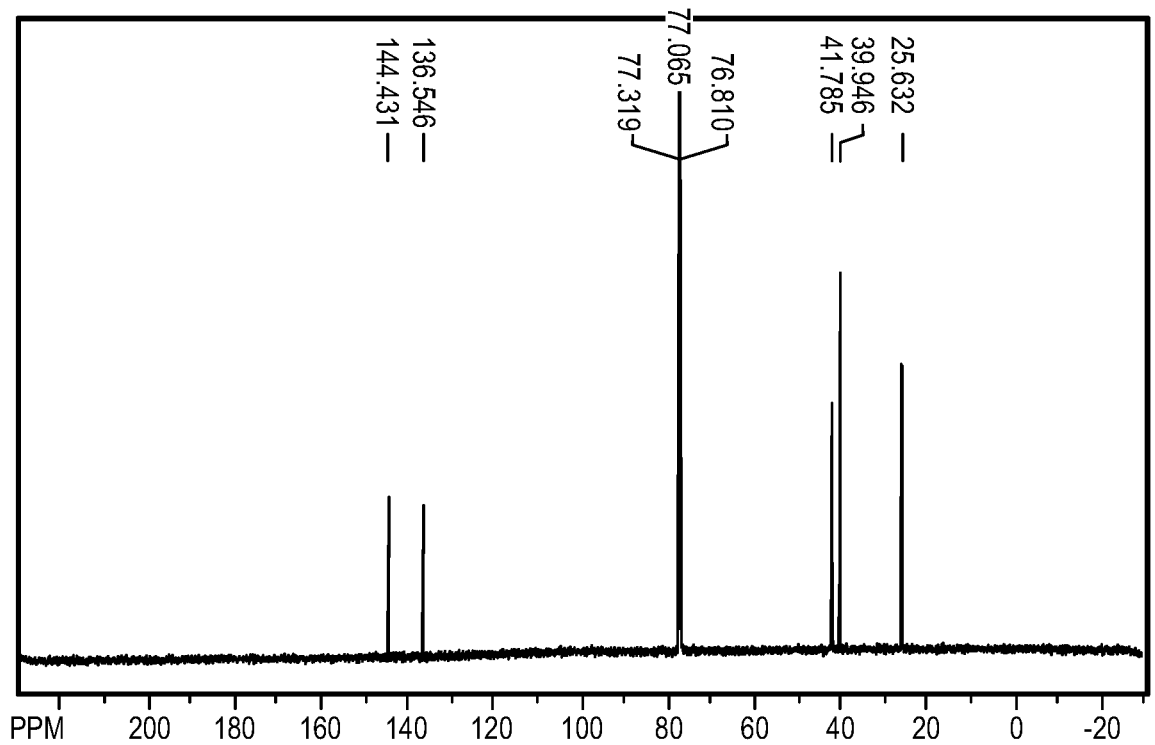
Figure 3:
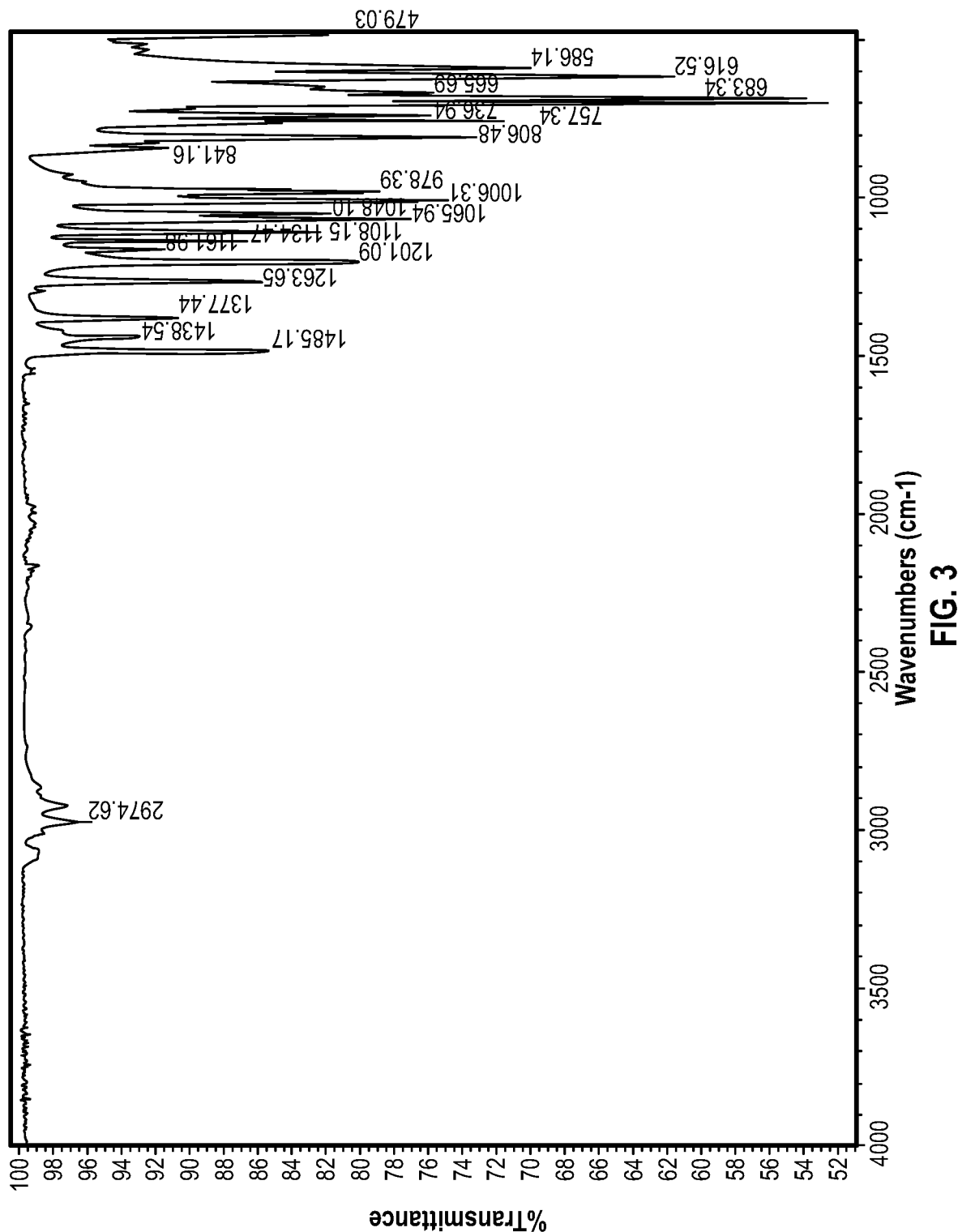
FIG. 3 is an infrared spectrum of 1,3,5-tris(halomethyl)-2,4,6-tris(α-bromoethyl)benzene.
Figure 4:
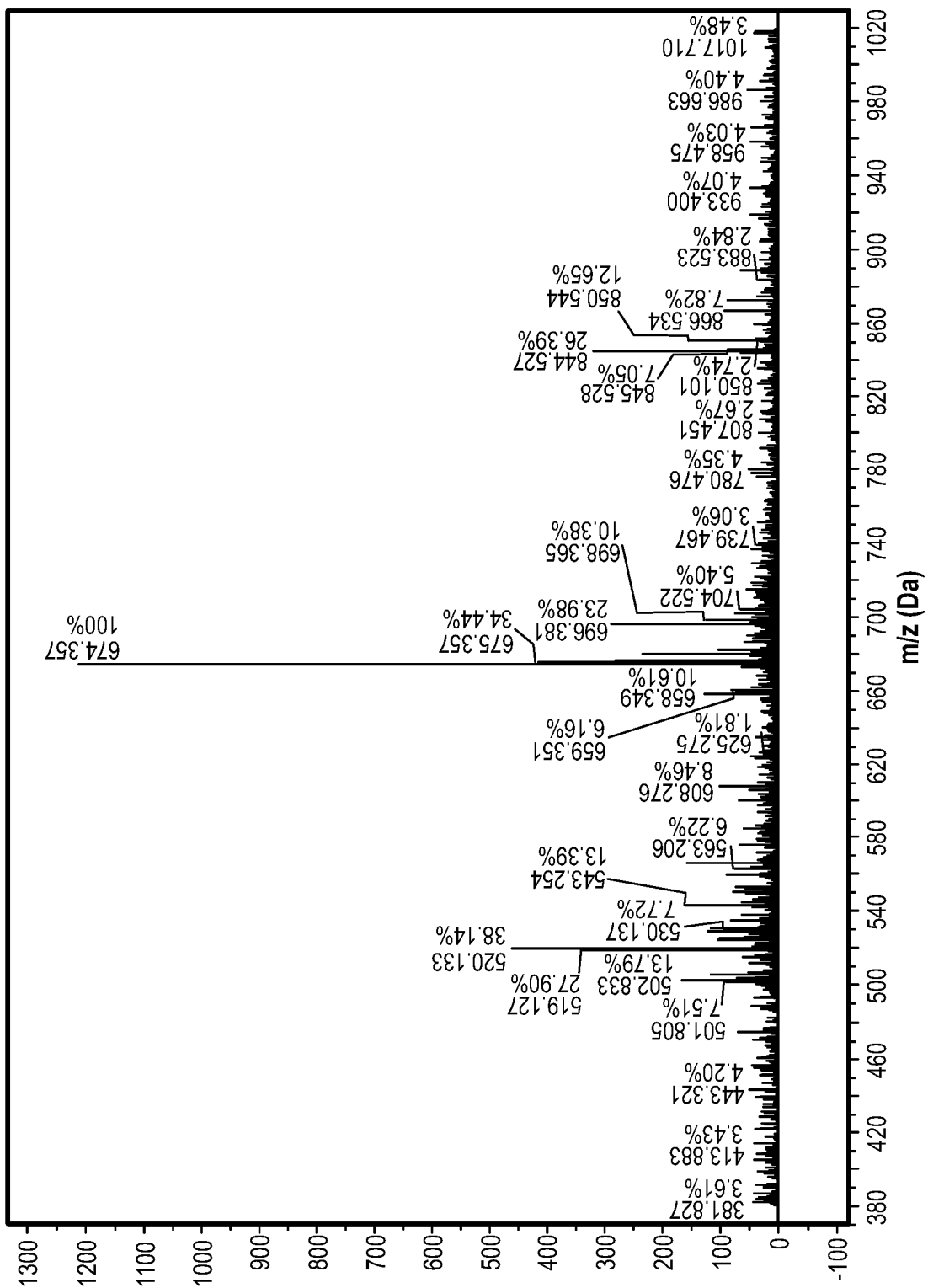
FIG. 4 is MALDI-TOF mass spectrometry data of 1,3,5-tris(halomethyl)-2,4,6-tris(α-bromoethyl)benzene.
Figure 5:
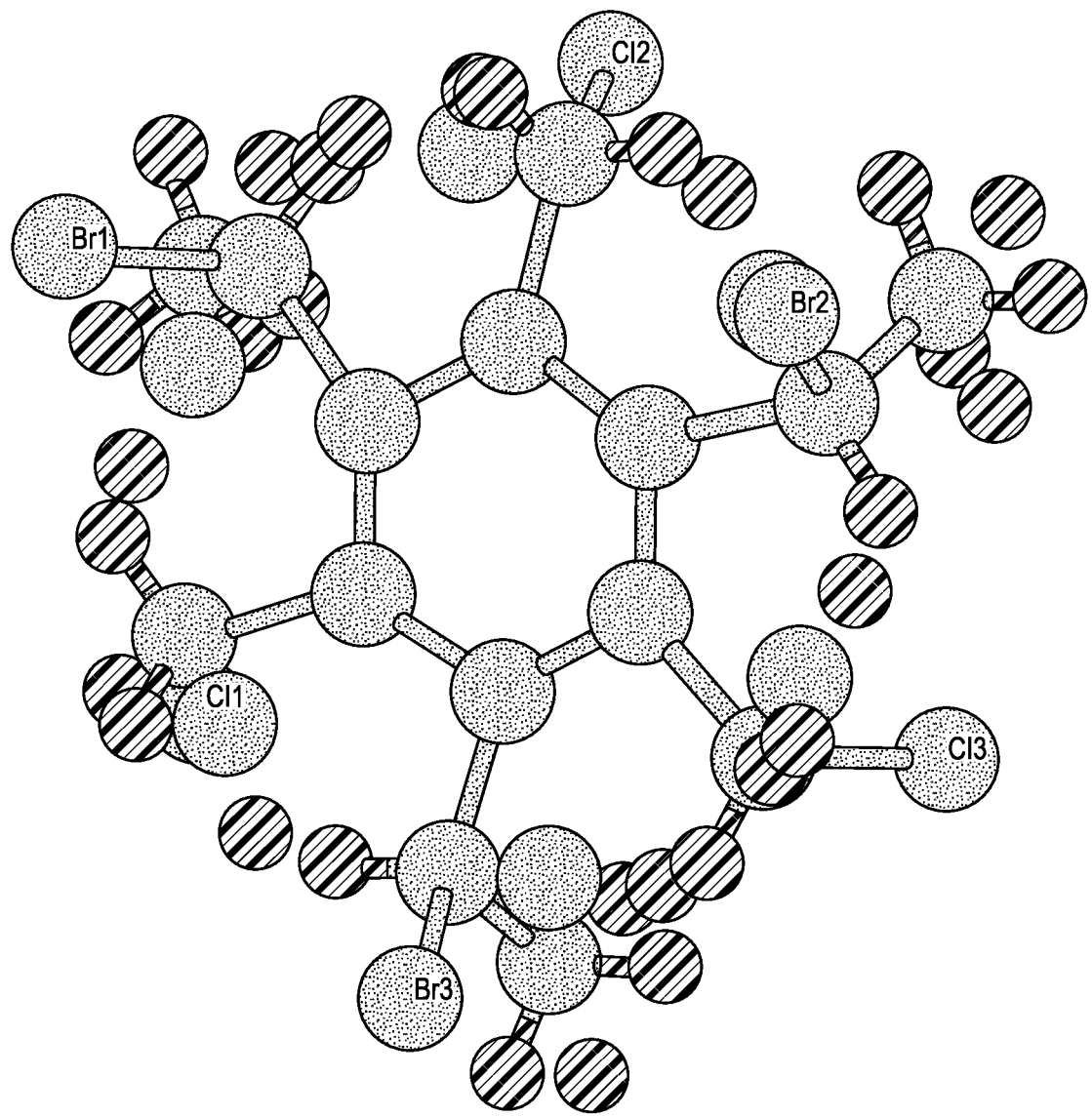
FIG. 5 is a depiction of the crystal structure of 1,3,5-tris(halomethyl)-2,4,6-tris(α-bromoethyl)benzene.

Compound C: 1,3,5-Tris(bromomethyl)-2,4,6-tris(α-chloroethyl)benzene. The title compound was synthesized by reacting Compound A or Compound B with excess N-bromosuccinimide (NBS) in CC14. In one example, Compound A was dissolved in CC14, and 3 molar equivalents of NBS were added. The reaction was heated to reflux, and 0.1 molar equivalents of AIBN were added. The title compound was isolated by aqueous workup and column chromatography. When the reaction was conducted with >6 molar equivalents of NBS, halide exchange of the benzylic chloride for bromides took place. FIGS. 1 and 2 are $^1$H and $^{13}$C NMR spectra of the title compound in CDCl$_3$, respectively. FIG. 3 is an infrared spectrum of the title compound. FIG. 4 shows Maldi-TOF mass spectrometry data of the title compound. FIG. 5 shows a depiction of the crystal structure of the title compound.

Compound D: 1,3,5-Tris(bromomethyl)-2,4,6-trivinylbenzene. The title compound was synthesized by reacting Compound C with excess potassium t-butoxide in t-butanol. Compound C was combined with 3 molar equivalents of potassium t-butoxide in t-butanol and reacted at 70° C. The product was isolated essentially quantitatively after aqueous workup. FTIR (not shown) showed the appearance of a new C=C stretch and a new C—H stretch centered at 1660 cm$^{-1}$ and 3084 cm$^{-1}$, respectively.

Figure 6:
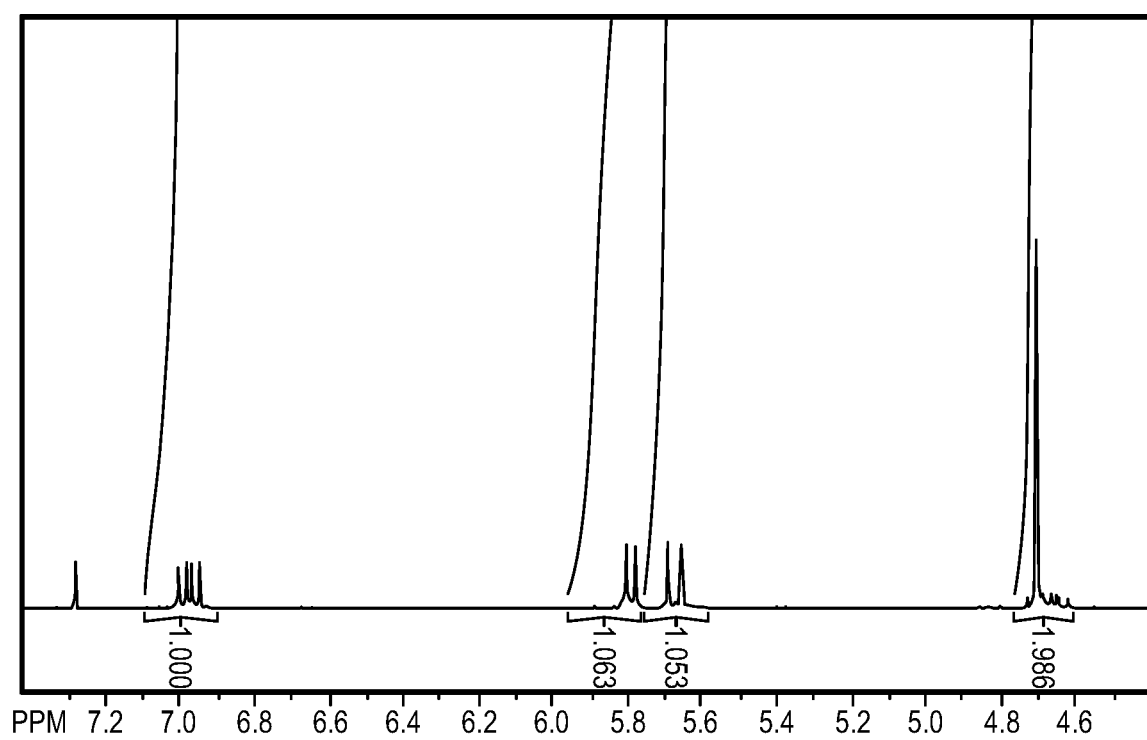
FIG. 6 is a $^1$H NMR spectrum of 1,3,5-tris(bromomethyl)-2,4,6-triepoxybenzene in CDCl$_3$.

Compound E: 1,3,5-Tris(bromomethyl)-2,4,6-triepoxybenzene. The title compound was synthesized by reacting Compound D with dimethyldioxirane in acetone. Compound D was first dissolved in methylene chloride and a solution of dimethyldioxirane in acetone was added. The dimethyldioxirane was prepared in situ by reacting potassium peroxymonosulfate (OXONE) with acetone. The reaction was continued until the C=C stretch was absent by FTIR. The title compound was obtained essentially quantitatively. Alternately, the title compound may be prepared by reacting Compound D with m-chloroperoxybenzoic acid (mCPBA). FIG. 6 is a $^1$H NMR spectrum of the title compound in CDCl$_3$.

Figure 7:
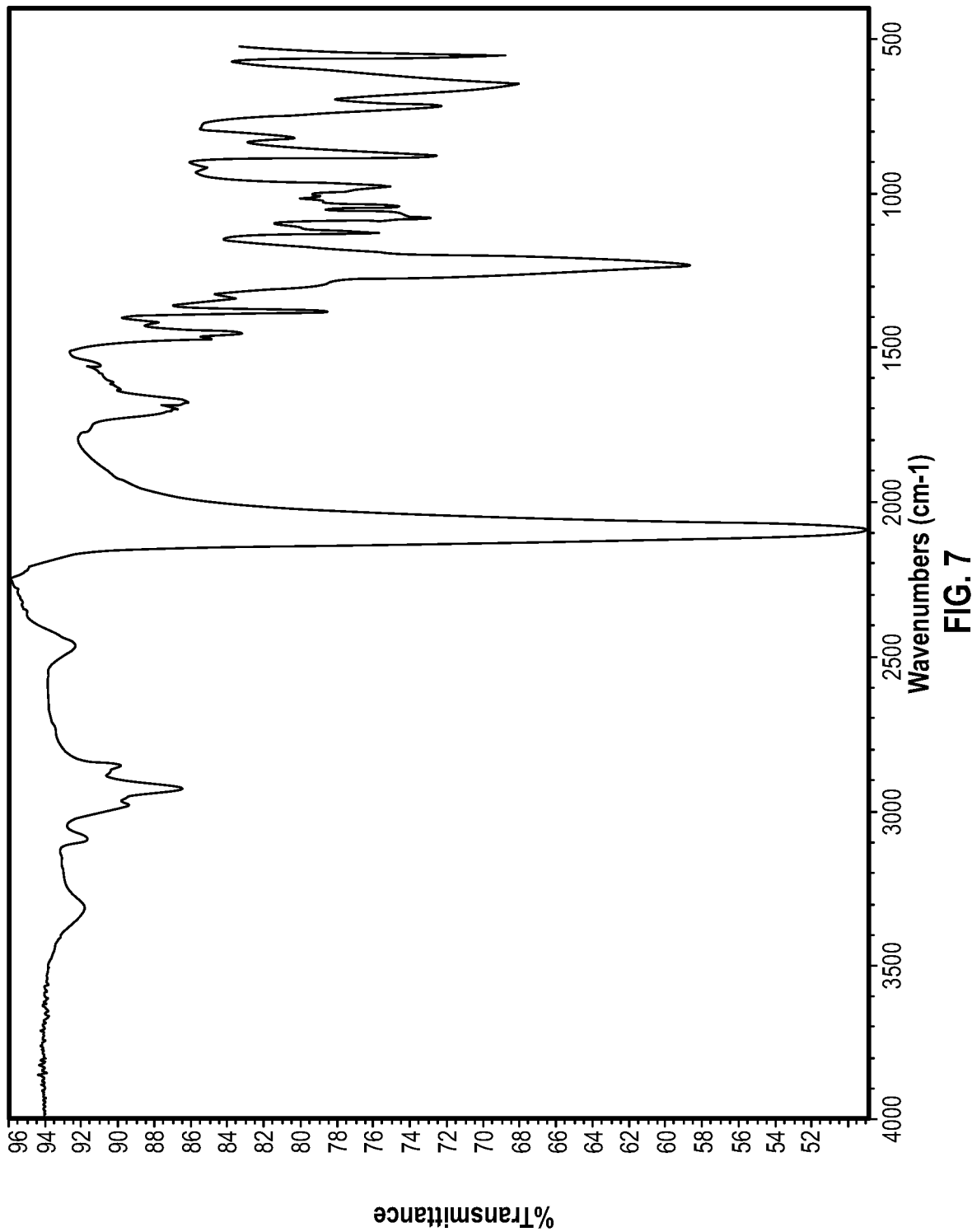
FIG. 7 is an infrared spectrum of 1,3,5-tris(azidomethyl)-2,4,6-triepoxybenzene.

Compound F: 1,3,5-Tris(azidomethyl)-2,4,6-triepoxybenzene. The title compound was synthesized by reacting Compound E with sodium azide in DMF at room temperature. CAUTION: NaN$_3$ may be explosive under some conditions and is highly toxic. No epoxide opening was observed. FIG. 7 is an infrared spectrum of the title compound.

Iron Binding. Hexasubstituted benzenes capable of binding iron (Fe$^{2+}$ and/or Fe$^{3+}$) were synthesized in accordance with Scheme 10 below.

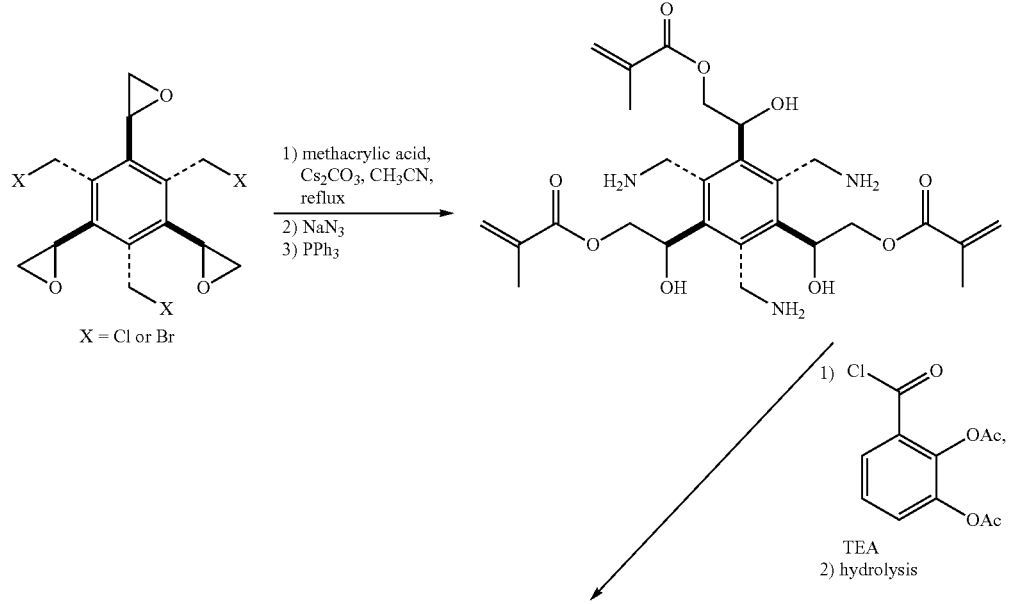

Scheme 10

-continued

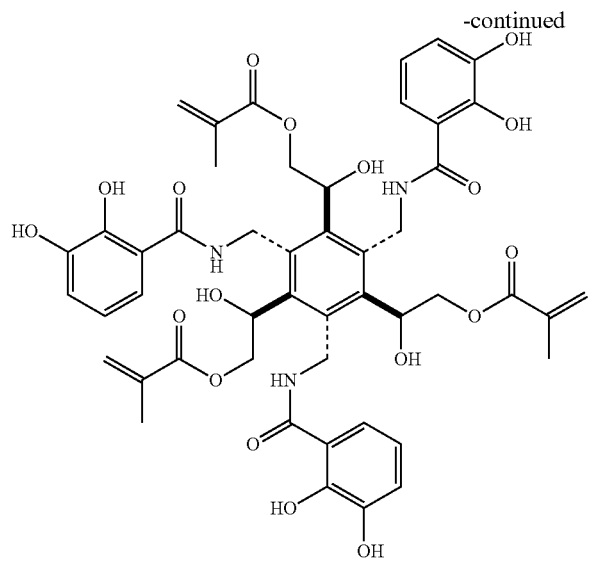

In brief, the epoxides of Compound E were nucleophilically opened by methacrylate in the presence of cesium carbonate and a polar aprotic solvent such as acetonitrile. Methacrylic acid was dissolved in acetonitrile and deprotonated with cesium carbonate. Compound E was heated with the cesium carboxylate in acetonitrile at reflux under inert atmosphere. The product was isolated by aqueous workup and column chromatography, and characterization by NMR, FTIR and mass spectrometry was performed.

Thereafter, the benzylic halides were displaced with sodium azide in a polar aprotic solvent, such as DMF. Reduction of the covalently bound azides with triphenylphosphine was then conducted in a THF/water mixture. The resulting amines were then acylated with 2,3-diacetoxybenzoyl chloride (2-5% molar excess) in the presence of a hindered amine base (5-10% molar excess), such as triethylamine. The acylated product was isolated by aqueous workup and column chromatography, and characterization by NMR, FTIR and mass spectrometry were performed. The acetate protecting groups may be removed by mild basic hydrolysis or in situ removal may occur when contacting a solution containing iron ions.

The acylated hexasubstituted benzene exhibited a linear response to increasing concentrations of iron ions in an aqueous solution, sometimes containing methanol or acetonitrile as a co-solvent to aid in solubility. The maximum absorbance intensity changed at various pH values. A buffer was used during the pH-dependence measurements (acetate, TRIS, MES and MOPS buffers were used). A 1:1 binding ratio of metal to catechol functional groups was determined by a Job plot.

Lithium Binding. Hexasubstituted benzenes capable of binding lithium ($Li^+$, particularly in hydrated form) were synthesized in accordance with Scheme 11 below.

Scheme 11

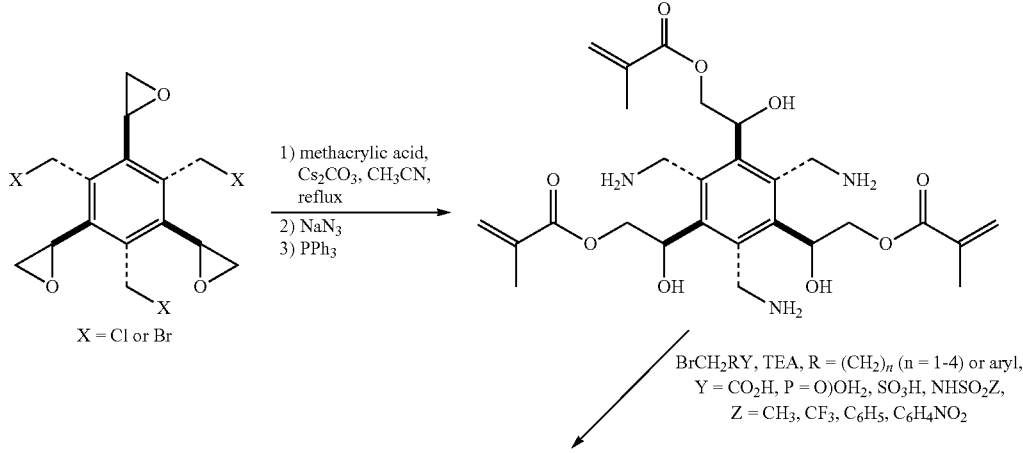

-continued

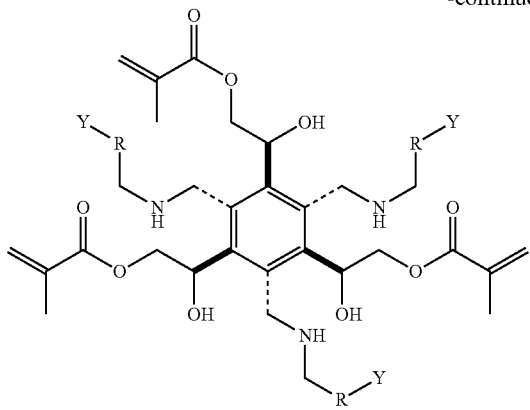

The synthesis was carried out in a similar manner to that described above for preparing an iron-binding compound, except a halocarboxylic acid, halosulfonic acid, halophosphonic acid, or halosulfonamide was employed to alkylate the amine groups.

Lithium sequestration was measured for the analogue with $R=(CH_2)_3$ and $Y=CO_2H$ in a methanol-water solution having a pH of 4.5 maintained with an acetate buffer. Addition of celestine blue dye afforded a color change from blue to purple. When back titration with lithium chloride was performed, the blue color returned, and the color intensity was proportional to the amount of added lithium. The change from purple to blue is believed to be indicative of competitive displacement of the dye from the hexasubstituted benzene by the lithium ions. Again, a linear increase in absorbance intensity was observed with increasing amounts of added lithium ions.

The same compound was also covalently bonded to a polymer macroparticulate. The macroparticulate-bound lithium-binding compound was then exposed to a lithium ion solution containing celestine blue dye at a pH of 4.5 maintained with an acetate buffer. Prior to adding of the macroparticulates to the lithium ion solution, the dye color was purple. Following addition of the macroparticulates, the color change was reversed to afford a blue color.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed

What is claimed is the following:

1. A hexasubstituted benzene having a structure of

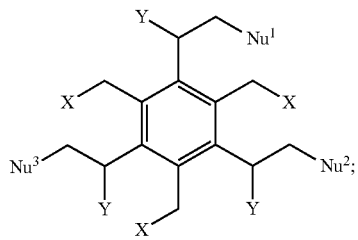

wherein $Nu^1$, $Nu^2$, and $Nu^3$ are each amines or a protected form thereof; Y is H or OH; and X is $N_3$ or a reaction product of $N_3$.

2. The hexasubstituted benzene of claim 1, wherein $Nu^1$, $Nu^2$, and $Nu^3$ are each different.

3. The hexasubstituted benzene of claim 2, wherein the amines are orthogonally protected.

4. The hexasubstituted benzene of claim 1, wherein the reaction product of $N_3$ is $NH_2$ or a surface-bound form thereof.

5. The hexasubstituted benzene of claim 1, wherein the reaction product of $N_3$ is a 1,2,3-triazole or a surface-bound form thereof.

6. The hexasubstituted benzene of claim 1, wherein at least one of $Nu^1$, $Nu^2$, and $Nu^3$ bears a binding functionality that undergoes molecular association with an analyte of interest.

7. The hexasubstituted benzene of claim 6, wherein the binding functionality is selected from the group consisting of a chelating ligand, a crown ether, a cryptand, a porphyrin, a calixarene, an analyte-sensitive dye, a pH-sensitive compound, an antibody, an enzyme, a protein, and a biological receptor.

8. The hexasubstituted benzene of claim 6, wherein at least one of $Nu^1$, $Nu^2$, and $Nu^3$ bears a detection functionality, wherein the detection functionality allows the molecular association of the analyte with the binding functionality to be detected spectroscopically or electrochemically.

9. The hexasubstituted benzene of claim 6, wherein at least one of $Nu^1$, $Nu^2$, and $Nu^3$ bears an additional functionality that alters a strength of the molecular association of the analyte with the binding functionality, the additional functionality being a pH buffer, a scavenger of a reactive species, or a functionality that increases or decreases electron density.

10. A modified surface comprising:
a base surface having a plurality of functionalities reactive with an amine or an azide; and
a reaction product of the base surface and a hexasubstituted benzene bearing an amine or an azide, the reaction product being covalently bonded to the base surface and having a structure of

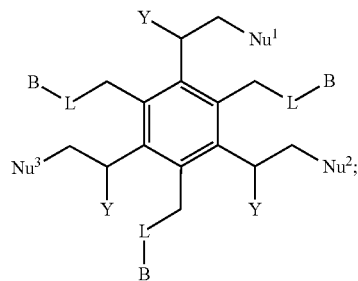

wherein B is the base surface; each L is a linking group connecting a benzylic carbon of the hexasubstituted benzene to the base surface via a reaction occurring between a functionality located upon the base surface and an azide or an amine located upon the benzylic carbon; $Nu^1$, $Nu^2$, and $Nu^3$ are each amines or a protected form thereof; and Y is H or OH.

11. The modified surface of claim 10, wherein $Nu^1$, $Nu^2$, and $Nu^3$ are each different.

12. The modified surface of claim 11, wherein the amines are orthogonally protected.

13. The modified surface of claim 10, wherein L comprises a cycloaddition reaction product of a benzylic azide.

14. The modified surface of claim 13, wherein the cycloaddition reaction product is a 1,2,3-triazole.

15. The modified surface of claim 10, wherein L comprises a secondary or tertiary benzylic amine reaction product or a secondary or tertiary benzylic amide reaction product of a primary benzylic amine.

16. The modified surface of claim 10, wherein at least one of $Nu^1$, $Nu^2$, and $Nu^3$ bears a binding functionality that undergoes molecular association with an analyte of interest.

17. The modified surface of claim 16, wherein the binding functionality is selected from the group consisting of a chelating ligand, a crown ether, a cryptand, a porphyrin, a calixarene, an analyte-sensitive dye, a pH-sensitive compound, an antibody, an enzyme, a protein, and a biological receptor.

18. The modified surface of claim 16, wherein at least one of $Nu^1$, $Nu^2$, and $Nu^3$ bears a detection functionality, wherein the detection functionality allows the molecular association of the analyte with the binding functionality to be detected spectroscopically or electrochemically.

19. The modified surface of claim 16, wherein at least one of $Nu^1$, $Nu^2$, and $Nu^3$ bears an additional functionality that alters a strength of the molecular association of the analyte with the binding functionality, the additional functionality being a pH buffer, a scavenger of reactive species, or a functionality that increases or decreases electron density.

20. A sensor comprising the modified surface of claim 16.

* * * * *